(12) United States Patent
Belmares et al.

(10) Patent No.: US 8,324,168 B2
(45) Date of Patent: Dec. 4, 2012

(54) METHODS FOR TREATING PAIN

(75) Inventors: Michael P. Belmares, Campbell, CA (US); Jonathan David Garman, San Jose, CA (US); Peter S. Lu, Palo Alto, CA (US); Michael W. Salter, Toronto (CA); Michael Tymianski, Toronto (CA)

(73) Assignee: NoNO Inc., Toronto, Ontario (CA)

( * ) Notice: Subject to any disclaimer, the term of this patent is extended or adjusted under 35 U.S.C. 154(b) by 0 days.

(21) Appl. No.: 12/553,096

(22) Filed: Sep. 3, 2009

(65) Prior Publication Data

US 2010/0062985 A1 Mar. 11, 2010

Related U.S. Application Data

(60) Provisional application No. 61/094,026, filed on Sep. 3, 2008.

(51) Int. Cl.
*C07K 14/435* (2006.01)
*A61K 38/16* (2006.01)

(52) U.S. Cl. ........ 514/18.3; 514/1.1; 514/1.2; 514/17.3; 530/300

(58) Field of Classification Search .................. None
See application file for complete search history.

(56) References Cited

U.S. PATENT DOCUMENTS

| | | | |
|---|---|---|---|
| 7,510,824 B2 | 3/2009 | Tymianski | |
| 7,595,297 B2 | 9/2009 | Tymianski | |
| 7,846,897 B2 | 12/2010 | Tymianski | |
| 7,858,322 B2 | 12/2010 | Tymianski et al. | |
| 8,008,253 B2 | 8/2011 | Tasker et al. | |
| 8,071,548 B2 | 12/2011 | Tymianski | |
| 8,080,518 B2 | 12/2011 | Tymianski et al. | |
| 2003/0050243 A1 | 3/2003 | Tymianski | |
| 2005/0059597 A1 | 3/2005 | Tymianski | |
| 2005/0164933 A1 | 7/2005 | Tymianski et al. | |
| 2008/0019975 A1 | 1/2008 | Gorman et al. | |
| 2008/0119412 A1 | 5/2008 | Tymianski et al. | |
| 2008/0227684 A1 | 9/2008 | Belmares et al. | |
| 2008/0274977 A1 | 11/2008 | Belmares et al. | |
| 2009/0036376 A1 | 2/2009 | Tasker et al. | |
| 2009/0062178 A1* | 3/2009 | Harrison | 514/2 |
| 2009/0062213 A1 | 3/2009 | Belmares et al. | |
| 2009/0131321 A1 | 5/2009 | Tymianski | |
| 2009/0176713 A1 | 7/2009 | Tymianski et al. | |
| 2009/0281037 A1 | 11/2009 | Tymianski | |
| 2010/0062985 A1 | 3/2010 | Belmares et al. | |
| 2010/0137224 A1 | 6/2010 | Tymianski | |
| 2010/0160240 A1 | 6/2010 | Gurd et al. | |
| 2010/0204100 A1* | 8/2010 | Johns et al. | 514/12 |
| 2011/0251182 A1 | 10/2011 | Sun et al. | |

FOREIGN PATENT DOCUMENTS

EP 1 884 521 A1 2/2008

OTHER PUBLICATIONS

Aarts 2002 (Science 298:846-850).*
Sweitzer 2004 (Journal of Pharmacology and Experimental Therapeutics 309:616-625).*
PCT International Preliminary Report on Patentability (Chapter I) of Mar. 8, 2011 for application PCT/US2009/055786.
International Search Report for PCT/US2009/055786 mailed Mar. 3, 2010.
Sun et al., "Effectiveness of PSD95 Inhibitors in Permanent and Transient Focal Ischemia in the Rat," Stroke, 39(9):2544-2553, (2008).
Supplementary European Search Report and European Search Opinion mailed Jul. 17, 2012 for application EP09812187.4.

* cited by examiner

*Primary Examiner* — Christine J Saoud
*Assistant Examiner* — Jon M Lockard
(74) *Attorney, Agent, or Firm* — Alston & Bird LLP

(57) ABSTRACT

The invention provides agents useful for treating pain. An exemplary agent comprises or consists of the a portion of a retroviral Tat protein. One such agent is the peptide Tat-NR2B9c. This peptide has previously been described as an agent for inhibiting damaging effects of stroke and similar conditions via inhibition of PSD95 interactions with NMDA receptors and/or NOS. The present application provides data showing that the Tat-NR2B9c peptides is effective in alleviation of pain. The alleviation of pain can be obtained at a dose of the peptide below the dose required to inhibit PSD-95 interactions with NMDAR or NOS.

19 Claims, 11 Drawing Sheets

FIGURE 1A

| Cat. # | TARGET | BATCH* | SPP. | n= | CONC. | % | †% INHIBITION -100 -50 0 50 100 |
|---|---|---|---|---|---|---|---|
| 200510 | Adenosine A₁ | 151494 | hum | 2 | 10 µM | -8 | |
| 200610 | Adenosine A₂ₐ | 151495 | hum | 2 | 10 µM | 0 | |
| 200720 | Adenosine A₃ | 151503 | hum | 2 | 10 µM | -22 | |
| 203500 | Adrenergic α₁, Non-Selective | 151722 | rat | 2 | 10 µM | -19 | |
| 203900 | Adrenergic α₂, Non-Selective | 151551 | rat | 2 | 10 µM | -5 | |
| 204010 | Adrenergic β₁ | 151527 | hum | 2 | 10 µM | 8 | |
| 205000 | Anaphylatoxin C5a | 151609 | hum | 2 | 10 µM | 15 | |
| 210110 | Angiotensin AT₂ | 151781 | hum | 2 | 10 µM | 12 | |
| 226700 | Benzodiazepine, Peripheral | 151814 | rat | 2 | 10 µM | -17 | |
| 212610 | Bradykinin B₂ | 151530 | hum | 2 | 10 µM | -7 | |
| 214510 | Calcium Channel L-Type, Benzothiazepine | 151496 | rat | 2 | 10 µM | 6 | |
| 214600 | Calcium Channel L-Type, Dihydropyridine | 151497 | rat | 2 | 10 µM | 5 | |
| 215000 | Calcium Channel L-Type, Phenylalkylamine | 151498 | rat | 2 | 10 µM | 4 | |
| ♦ 216000 | Calcium Channel N-Type | 151744 | rat | 2 | 10 µM | 108 | |
| 217500 | Chemokine CCR1 | 151506 | hum | 2 | 10 µM | -15 | |
| ♦ 244500 | Chemokine CXCR2 (IL-8Rᵦ) | 152328 | hum | 2 | 10 µM | 77 | |
| 218010 | Cholecystokinin CCK₁ (CCKₐ) | 152108 | hum | 2 | 10 µM | -11 | |
| 219100 | Colchicine | 151615 | rat | 2 | 10 µM | -10 | |
| 219500 | Dopamine D₁ | 151531 | hum | 2 | 10 µM | 2 | |
| 219700 | Dopamine D₂ₛ | 151533 | hum | 2 | 10 µM | 1 | |
| 224010 | Endothelin ETₐ | 151508 | hum | 2 | 10 µM | 1 | |
| 226500 | GABAₐ, Agonist Site | 151572 | rat | 2 | 10 µM | 2 | |
| 226600 | GABAₐ, Benzodiazepine, Central | 152561 | rat | 2 | 10 µM | 12 | |
| 226810 | GABAₐ, Chloride Channel, TBOB | 151537 | rat | 2 | 10 µM | 4 | |
| 228510 | GABAᵦ, Non-Selective | 151952 | rat | 2 | 10 µM | 0 | |
| 228600 | GABAᵦ₁ₐ | 151853 | hum | 2 | 10 µM | -11 | |
| 228700 | GABAᵦ₁ᵦ | 151575 | hum | 2 | 10 µM | 27 | |
| 231600 | Galanin GAL2 | 152193 | hum | 2 | 10 µM | -22 | |
| 232600 | Glutamate, AMPA | 151576 | rat | 2 | 10 µM | -2 | |

FIGURE 1B

| Cat. # | TARGET | BATCH* | SPP. | n= | CONC. | †% INHIBITION % |
|---|---|---|---|---|---|---|
| 232700 | Glutamate, Kainate | 151577 | rat | 2 | 10 μM | -12 |
| 232810 | Glutamate, NMDA, Agonism | 151578 | rat | 2 | 10 μM | 6 |
| 232910 | Glutamate, NMDA, Glycine | 151579 | rat | 2 | 10 μM | 10 |
| 233000 | Glutamate, NMDA, Phencyclidine | 151580 | rat | 2 | 10 μM | -21 |
| 234000 | Glutamate, NMDA, Polyamine | 151619 | rat | 2 | 10 μM | 28 |
| 235010 | Glutamate, Non-Selective | 152191 | rat | 2 | 10 μM | 22 |
| 239000 | Glycine, Strychnine-Sensitive | 151620 | rat | 2 | 10 μM | 18 |
| 239610 | Histamine $H_1$ | 151538 | hum | 2 | 10 μM | 2 |
| 239710 | Histamine $H_2$ | 151539 | hum | 2 | 10 μM | 0 |
| 239810 | Histamine $H_3$ | 151540 | hum | 2 | 10 μM | -28 |
| 239900 | Histamine $H_4$ | 151541 | hum | 2 | 10 μM | -11 |
| 241000 | Imidazoline $I_2$, Central | 151581 | rat | 2 | 10 μM | -17 |
| 241100 | Imidazoline $I_2$, Peripheral | 152162 | rat | 2 | 10 μM | 5 |
| 243510 | Interleukin IL-1 | 151547 | mouse | 2 | 10 μM | 3 |
| 243700 | Interleukin IL-2 | 151710 | mouse | 2 | 10 μM | 6 |
| 244100 | Interleukin IL-6 | 151711 | hum | 2 | 10 μM | -10 |
| 252610 | Muscarinic $M_1$ | 151513 | hum | 2 | 10 μM | 8 |
| 252710 | Muscarinic $M_2$ | 151514 | hum | 2 | 10 μM | 4 |
| 252810 | Muscarinic $M_3$ | 151515 | hum | 2 | 10 μM | -25 |
| 257010 | Neuropeptide Y $Y_1$ | 151516 | hum | 2 | 10 μM | 0 |
| 257110 | Neuropeptide Y $Y_2$ | 151517 | hum | 2 | 10 μM | 6 |
| 258010 | Neurotensin $NT_1$ | 152160 | hum | 2 | 10 μM | 28 |
| 260110 | Opiate δ (OP1, DOP) | 151542 | hum | 2 | 10 μM | -4 |
| 260210 | Opiate κ (OP2, KOP) | 151543 | hum | 2 | 10 μM | 5 |
| 260410 | Opiate μ (OP3, MOP) | 151544 | hum | 2 | 10 μM | 4 |
| 260600 | Orphanin $ORL_1$ | 152161 | hum | 2 | 10 μM | 43 |
| 265800 | Potassium Channel [$SK_{Ca}$] | 151632 | rat | 2 | 10 μM | 17 |
| 265900 | Potassium Channel HERG | 151518 | hum | 2 | 10 μM | 7 |
| 271110 | Serotonin (5-Hydroxytryptamine) 5-$HT_{1A}$ | 151594 | hum | 2 | 10 μM | -12 |
| 271650 | Serotonin (5-Hydroxytryptamine) 5-$HT_{2A}$ | 151502 | hum | 2 | 10 μM | 1 |

FIGURE 1C

| Cat. # | TARGET | BATCH* | SPP. | n= | CONC. | †% INHIBITION % |
|---|---|---|---|---|---|---|
| 271910 | Serotonin (5-Hydroxytryptamine) 5-HT$_3$ | 151598 | hum | 2 | 10 µM | -4 |
| 272100 | Serotonin (5-Hydroxytryptamine) 5-HT$_{5A}$ | 151601 | hum | 2 | 10 µM | -12 |
| 272200 | Serotonin (5-Hydroxytryptamine) 5-HT$_6$ | 151602 | hum | 2 | 10 µM | -3 |
| 279510 | Sodium Channel, Site 2 | 151606 | rat | 2 | 10 µM | -2 |
| 226400 | Transporter, GABA | 151536 | rat | 2 | 10 µM | 6 |
| 239100 | Transporter, Glycine | 152079 | rat | 2 | 10 µM | -8 |
| 287010 | Vasoactive Intestinal Peptide VIP$_1$ | 151520 | hum | 2 | 10 µM | -1 |
| 287520 | Vasopressin V$_{1A}$ | 151649 | hum | 2 | 10 µM | 3 |

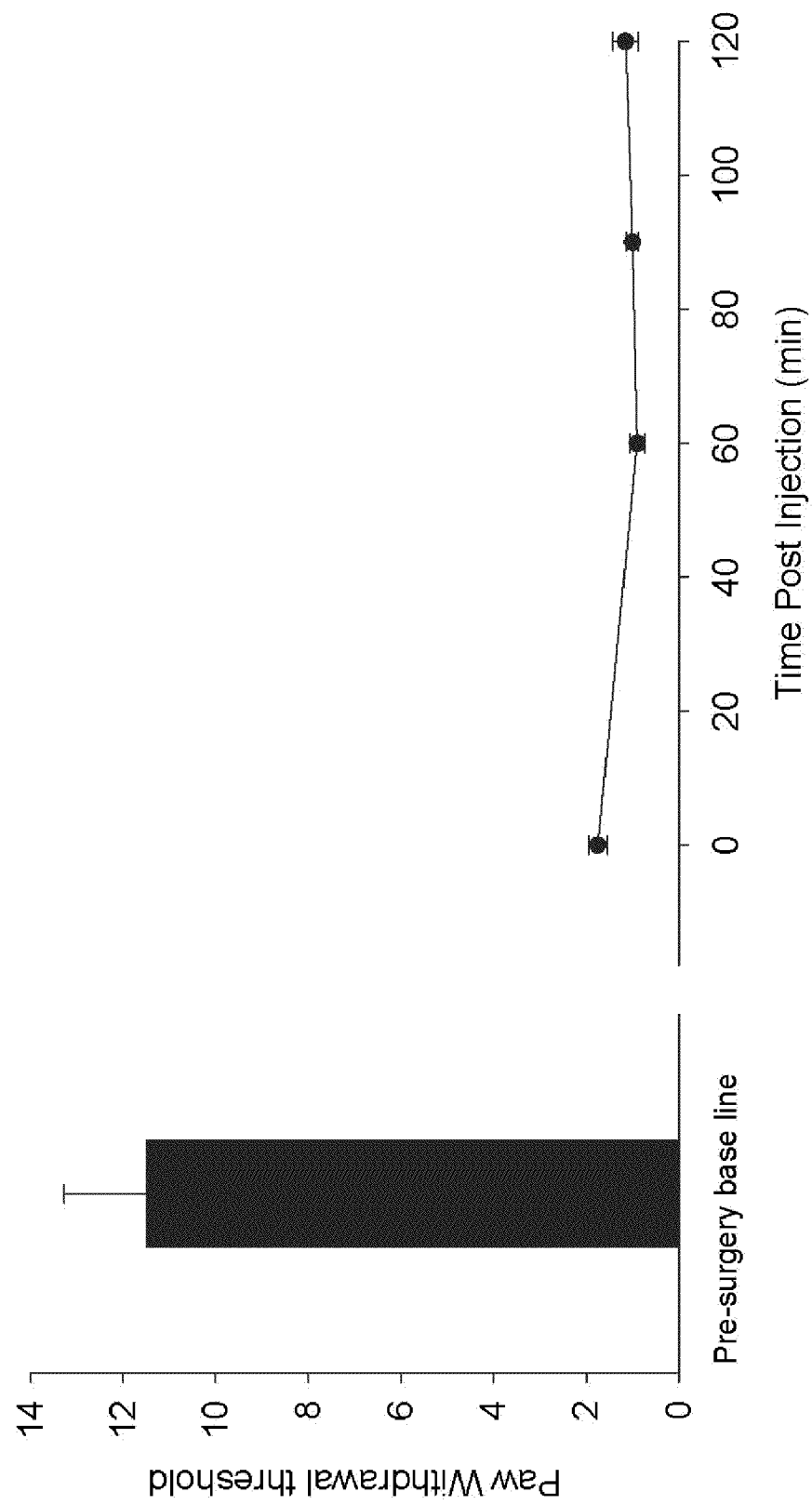

A

B

METHODS FOR TREATING PAIN

CROSS REFERENCE TO RELATED APPLICATIONS

This application claims the benefit of U.S. Provisional Patent App. No. 61/094,026 filed Sep. 3, 2008, incorporated by reference herein in its entirety for all purposes.

REFERENCE TO A SEQUENCE LISTING

A Sequence Listing filed herewith in computer-readable format, contained in file 026373-001010US_SEQLST.txt, which is 5,772 bytes is size, and was created on Sep. 2, 2009, is hereby incorporated by reference in its entirety.

BACKGROUND OF THE INVENTION

Pain is a complex phenomenon that includes a sensory experience that usually involves an awareness of a noxious stimulus or bodily harm. Individuals experience pain through diverse causes, from various daily hurts and aches, through more serious injuries or illnesses.

Despite its unpleasantness, pain is an important part of the existence of humans and other animals; in fact, it is vital to healthy survival. Pain is part of the body's defense system, triggering mental and physical behavior to end the painful experience. It promotes learning so that repetition of the painful situation will be less likely. Pain encourages an organism to disengage from the noxious stimulus associated with the pain. Preliminary pain can serve to indicate that an injury is imminent, such as the ache from a soon-to-be-broken bone. Pain may also promote the healing process, since most organisms will protect an injured region in order to avoid further pain.

A plethora of molecular mediators have been implicated in pain perception, including sodium, potassium and calcium ion channels. A huge diversity of analgesic drugs are in use today. Examples include non-steroidal anti-inflammatory drugs (NSAIDs) such as the salicylates, narcotic drugs such as morphine, synthetic drugs with narcotic properties such as tramadol, and various others.

BRIEF SUMMARY OF THE INVENTION

The invention among other things provides pain-relieving agents that for example comprise an amino acid sequence comprising YGRKKRRQRRRKLSSIESDV (SEQ ID NO:1) or a variant having fewer than ten deletions, substitutions or insertions of the sequence, or a peptidomimetic of the sequence or variant. The invention also includes a method of treating pain, comprising administering an agent of the invention to a patient experiencing or at risk of pain in a regime effective to treat or effect prophylaxis of the pain. Optionally, the dose is below 1 mg/kg. Optionally, the dose is $10^{-5}$ to $10^{-1}$ mg/kg. Optionally, the patient is not experiencing at least one disease or disorder selected from the group consisting of stroke, epilepsy, hypoxia, traumatic injury to the CNS, Alzheimer's disease, and Parkinson's disease. Optionally, the patient is not or is not believed to be suffering from any of these diseases. Optionally, the pain is at a peripheral site. Optionally, the pain is in the CNS. Optionally, the peptide or peptidomimetic is administered peripherally. Optionally, the peptide or peptidomimetic is administered intrathecally. Optionally, the treatment or prophylaxis of pain is effected by binding of the peptide or peptidomimetic to an N-type calcium channel.

The invention also includes agents that comprise or consist of a tat peptide having an amino acid sequence comprising YGRKKRRQRRR (SEQ ID NO:2) or a variant thereof having fewer than 4 deletions, substitutions or insertions of the sequence or a peptidomimetic of the tat peptide or variant a method of treating pain, comprising administering such peptides to a patient experiencing or at risk of pain in a regime effective to treat or effect prophylaxis of the pain. Optionally, the tat peptide is not linked to NMDAR 2B 9C. Optionally, the tat peptide is not linked to an inhibitor of PSD95-NMDAR interactions. Optionally, the tat peptide is linked to NMDAR 2B 9C. Optionally, the administered tat peptide does not enter the CNS in detectable amounts. Optionally, the regime predominantly results in inhibition of N-type calcium channels rather than inhibition of PSD-95 interactions with NMDAR or NOS.

BRIEF DESCRIPTION OF THE DRAWINGS

FIGS. 1A, B, C: Results of a receptor binding/inhibition study assessing the ability of the peptide Tat-NR2B9c (YGRKKRRQRRRKLSSIESDV, SEQ ID NO:1) to inhibit binding of various radiolabeled ligands to cellular receptors.

FIG. 3: Tat-NR2B9c reverses pain hypersensitivity in rats after peripheral nerve injury in a dose-dependent manner. FIG. 3C: Intravenous administration of higher doses of Tat-NR2B9c (10 mg/kg i.v.) showed no effect on pain hypersensitivity after peripheral nerve injury. Paw withdrawal threshold was measured immediately prior to Tat-NR2B9c administration (time=0) and then 60, 90 and 120 mins later (* indicates $p<0.05$ as compared with t=0).

FIG. 5A shows the effect of Tat-NR2B9c (100 μM) and ω-conotoxin (1 μM) on calcium current in cultured DRG neurons. FIG. 5B shows the nifedipine inhibition of DRG calcium current in the presence of Tat-NR2B9c (100 μM intracellular).

DETAILED DESCRIPTION OF THE INVENTION

I. Definitions

Figure 2:
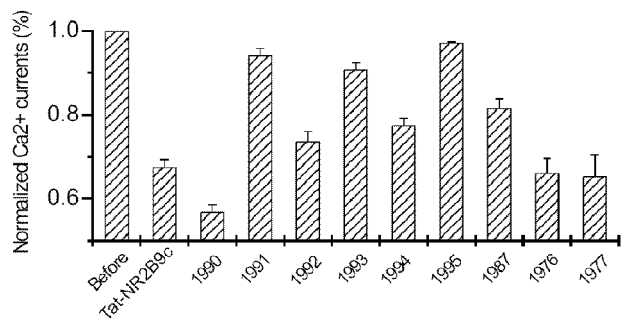
FIG. 2: Effect of applying various peptides on the amplitude of N-type calcium currents (upper) or whole cell currents (lower) in DRG neurons. "Before": normalized amplitude of calcium currents just before administration of peptide; Tat-NR2B9c:YGRKKRRQRRRKLSSIESDV (SEQ ID NO:1); 1990: a Tat peptide YGRKKRRQRRR (SEQ ID NO:2); 1991: peptide 2B9c (KLSSIESDV, SEQ ID NO:3); peptide Tat-NR2B9c:YGRKKRRQRRRKLSSIESDV (SEQ ID NO:1); 1992: peptide Tat-NR2B9c-AA (YGRKKRRQRRRKLSSIEADA, SEQ ID NO:4); 1993: peptide F-Tat-NR2B9c (FGRKKRRQRRRKLSSIESDV, SEQ ID NO:5); 1994: peptide Tat-NR2B9c K to A:YGRKKRRQRRRALSSIESDV, SEQ ID NO:6); 1995: peptide F-Tat-NR2B9c K to A (FGRKKRRQRRRALSSIESDV, SEQ ID NO:7); 1987: D-isomer of Tat-NR2B9c; 1976: YGRKKRRQRRRKLSSIESDX where X=norvaline (SEQ ID NO:9); 1977: YGRKKRRQRRRKLSSIESDX where X=L-t-butyl-glycine (SEQ ID NO:10).
Figure 2:
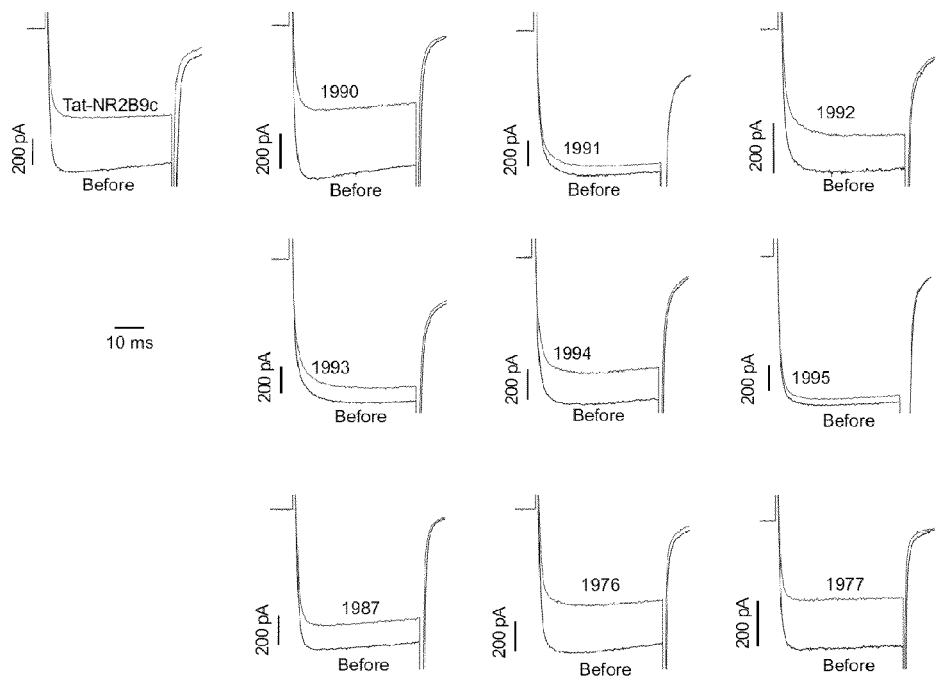

A "fusion polypeptide" refers to a composite polypeptide, i.e., a single contiguous amino acid sequence, made up of two (or more) distinct, heterologous polypeptides which are not normally fused together as in the amino acid sequence of the fusion peptide.

The term "PDZ domain" refers to a modular protein domain of about 90 amino acids, characterized by significant sequence identity (e.g., at least 60%) to the brain synaptic protein PSD-95, the *Drosophila* septate junction protein Discs-Large (DLG), and the epithelial tight junction protein ZO1 (ZO1). PDZ domains are also known as Discs-Large homology repeats ("DHRs") and GLGF repeats. PDZ domains generally appear to maintain a core consensus sequence (Doyle, D. A., 1996, *Cell* 85: 1067-76). Exemplary PDZ domain-containing proteins and PDZ domain sequences disclosed in U.S. application Ser. No. 10/714,537, which is herein incorporated by reference in its entirety.

The term "PL protein" or "PDZ Ligand protein" refers to a naturally occurring protein that forms a molecular complex with a PDZ-domain, or to a protein whose carboxy-terminus, when expressed separately from the full length protein (e.g., as a peptide fragment of 3-25 residues, e.g. 3, 4, 5, 8, 9, 10, 12, 14 or 16 residues), forms such a molecular complex. The molecular complex can be observed in vitro using the "A assay" or "G assay" described, e.g., in U.S. application Ser. No. 10/714,537, or in vivo.

The term "NMDA receptor," or "NMDAR," refers to a membrane associated protein that is known to interact with NMDA. The term thus includes the various subunit forms described in the Background Section. Such receptors can be human or non-human (e.g., mouse, rat, rabbit, monkey).

A "PL motif" refers to a short motif of 3, 4, 5, 6, 7, 8, 9, 10, 12, 14, 16, 20 or 25 contiguous amino acids that can bind to the PDZ domain of a PDZ protein. for example, C-terminal PL sequences can be found at the C-terminus of a PL protein (e.g., the last 3, 4, 5, 6, 7, 8, 9, 10, 12, 14, 16, 20 or 25 contiguous C-terminal residues of the PL protein). Other PL motifs can be found internally within a protein ("internal PL sequence").

A "PL peptide" is a peptide of comprising or consisting of, or otherwise based on, a PL motif that specifically binds to a PDZ domain.

A "peptidomimetic" refers to a synthetic chemical compound which has substantially the same structural and/or functional characteristics of a peptide consisting of natural amino acids. The peptidomimetic can contain entirely synthetic, non-natural analogues of amino acids, or can be a chimeric molecule of partly natural peptide amino acids and partly non-natural analogs of amino acids. The peptidomimetic can also incorporate any amount of natural amino acid conservative substitutions as long as such substitutions also do not substantially alter the mimetic's structure and/or inhibitory or binding activity. Polypeptide mimetic compositions can contain any combination of nonnatural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. In a peptidomimetic of a bifunctional peptide comprising a tat peptide and a second therapeutic peptide, either the tat peptide or the second peptide or both can be a peptidomimetic. In addition, polypeptides can have peptidomimetic bonds, such as N-methylated bonds ($-N(CH_3)-CO-$), ester bonds ($-C(R)H-C-O-O-C(R)-N-$), ketomethylen bonds ($-CO-CH_2-$), aza bonds ($-NH-N(R)-CO-$), wherein R is any alkyl, e.g., methyl, carba bonds ($-CH_2-NH-$), hydroxyethylene bonds ($-CH(OH)-CH_2-$), thioamide bonds ($-CS-NH-$), olefinic double bonds ($-CH=CH-$), retro amide bonds ($-NH-CO-$), peptide derivatives ($-N(R)-CH_2-CO-$), wherein R is the "normal" side chain, naturally presented on the carbon atom. These modifications can occur at any of the bonds along the peptide chain and even at several (2-3) at the same time. For example, a peptide can include an ester bond. A polypeptide can also incorporate a reduced peptide bond, i.e., $R_1-CH_2-NH-R_2$, where $R_1$ and $R_2$ are amino acid residues or sequences. A reduced peptide bond may be introduced as a dipeptide subunit. Such a polypeptide would be resistant to protease activity, and would possess an extended half-live in vivo. The affinity elements can also be peptoids (N-substituted glycines), in which the sidechains are appended to nitrogen atoms along the molecule's backbone, rather than to the α-carbons, as in amino acids.

The term "specific binding" refers to binding between two molecules, for example, a ligand and a receptor, characterized by the ability of a molecule (ligand) to associate with another specific molecule (receptor) even in the presence of many other diverse molecules, i.e., to show preferential binding of one molecule for another in a heterogeneous mixture of molecules. Specific binding of a ligand to a receptor is also evidenced by reduced binding of a detectably labeled ligand to the receptor in the presence of excess unlabeled ligand (i.e., a binding competition assay).

An "agent" or "active agent" is generally a compound that has or may have a desired activity. Unless otherwise specified, the desired activity is a therapeutic or pharmacological activity such as alleviation or prophylaxis of pain. Agents include compounds that are known drugs, compounds for which pharmacological activity has been identified but which are undergoing further therapeutic evaluation, and compounds that are members of collections and libraries that are to be screened for a pharmacological activity. For example, an active peptide is an active agent that is a peptide. An active chimeric agent comprises an active agent linked to an internalization peptide. The term "agent" is intended to include not only the indicated agent but also a functionally active analog, variant, or derivative of the indicated agent. An "internalization agent" need not have a therapeutic effect but can allow intracellular delivery of an attached therapeutic agent into cells (and/or delivery across the blood brain barrier).

A "therapeutic" or "pharmacological" activity means that an active agent exhibits an activity in a screening system that indicates that the active agent is or may be useful in the prophylaxis or treatment of pain or a disease, e.g., a disease associated with pain. The screening system can be in vitro, cellular, animal or human. Agents can be described as having therapeutic or pharmacological activity notwithstanding that further testing may be required to establish actual prophylactic or therapeutic utility in treatment of a disease.

"Significant" refers to a p-value that is <0.05, preferably <0.01 and most preferably <0.001.

II. General

The invention provides agents useful for treating pain. An exemplary agent comprises or consists of the peptide Tat-NR2B9c (YGRKKRRQRRRKLSSIESDV, SEQ ID NO:1). This peptide has previously been described as an agent for inhibiting damaging effects of stroke and similar conditions via inhibition of PSD95 interactions with NMDA receptors and/or NOS. The present application provides data showing that the Tat-NR2B9c peptides is effective in alleviation of pain. The alleviation of pain can be obtained at a dose of the peptide below the dose required to inhibit PSD-95 interactions with NMDAR or NOS.

Although an understanding of mechanism is not required for practice of the invention, the efficacy of Tat-NR2Bc peptide in treatment or prophylaxis of pain appears to be through a mechanism other than inhibition of PSD95 interactions with NMDAR and NOS. One possible mechanism is via binding to N-type calcium channels. The non-PSD95 mediated mechanism of action is effective at a lower therapeutic dose of Tat-NR2Bc than previously described methods of treatment of neurological diseases such as stroke and epilepsy, which methods involve the inhibition of PSD95 interactions with Tat-NR2B9c.

III. Pain

In its broadest usage, "pain" refers to an experiential phenomenon that is highly subjective to the individual experiencing it, and is influenced by the individual's mental state, including environment and cultural background. "Physical" pain can usually be linked to a stimulus perceivable to a third party that is causative of actual or potential tissue damage. In this sense, pain can be regarded as a "sensory and emotional experience associated with actual or potential tissue damage, or described in terms of such damage," according to the International Association for the Study of Pain (IASP). However, some instances of pain have no perceivable cause. For example, psychogenic pain, including exacerbation of a pre-existing physical pain by psychogenic factors or syndromes of a sometimes-persistent, perceived pain in persons with psychological disorders without any evidence of a perceivable cause of pain.

1) Types of Pain

Pain includes nociceptive pain, neuropathic/neurogenic pain, breakthrough pain, allodynia, hyperalgesia, hyperesthesia, dysesthesia, paresthesia, hyperpathia, phantom limb pain, psychogenic pain, anesthesia dolorosa, neuralgia, neuritis. Other categorizations include malignant pain, anginal pain, and/or idiopathic pain, complex regional pain syndrome I, complex regional pain syndrome II. Types and symptoms of pain need not be mutually exclusive. These terms are intended as defined by the IASP.

Nociceptive pain is initiated by specialized sensory nociceptors in the peripheral nerves in response to noxious stimuli, encoding noxious stimuli into action potentials. Nociceptors, generally on A-δ and C fibers, are free nerve endings that terminate just below the skin, in tendons, joints, and in body organs. The dorsal root ganglion (DRG) neurons provide a site of communication between the periphery and the spinal cord. The signal is processed through the spinal cord to the brainstem and thalamic sites and finally to the cerebral cortex, where it usually (but not always) elicits a sensation of pain. Nociceptive pain can result from a wide variety of a chemical, thermal, biological (e.g., inflammatory) or mechanical events that have the potential to irritate or damage body tissue, which are generally above a certain minimal threshold of intensity required to cause nociceptive activity in nociceptors.

Neuropathic pain is generally the result of abnormal functioning in the peripheral or central nervous system, giving rise to peripheral or central neuropathic pain, respectively. Neuropathic pain is defined by the International Association for the Study of Pain as pain initiated or caused by a primary lesion or dysfunction in the nervous system. Neuropathic pain often involves actual damage to the nervous system, especially in chronic cases. Inflammatory nociceptive pain is generally a result of tissue damage and the resulting inflammatory process. Neuropathic pain can persist well after (e.g., months or years) beyond the apparent healing of any observable damage to tissues.

In cases of neuropathic pain, sensory processing from an affected region can become abnormal and innocuous stimuli (e.g., thermal, touch/pressure) that would normally not cause pain may do so (i.e., allodynia) or noxious stimuli may elicit exaggerated perceptions of pain (i.e., hyperalgesia) in response to a normally painful stimulus. In addition, sensations similar to electric tingling or shocks or "pins and needles" (i.e., paresthesias) and/or sensations having unpleasant qualities (i.e., dysesthesias) may be elicited by normal stimuli. Breakthrough pain is an aggravation of pre-existing chronic pain. Hyperpathia is a painful syndrome resulting from an abnormally painful reaction to a stimulus. The stimulus in most of the cases is repetitive with an increased pain threshold, which can be regarded as the least experience of pain which a patient can recognize as pain.

Examples of neuropathic pain include tactile allodynia (e.g., induced after nerve injury) neuralgia (e.g., post herpetic (or post-shingles) neuralgia, trigeminal neuralgia), reflex sympathetic dystrophy/causalgia (nerve trauma), components of cancer pain (e.g., pain due to the cancer itself or associated conditions such as inflammation, or due to treatment such as chemotherapy, surgery or radiotherapy), phantom limb pain, entrapment neuropathy (e.g., carpal tunnel syndrome), and neuropathies such as peripheral neuropathy (e.g., due to diabetes, HIV, chronic alcohol use, exposure to other toxins (including many chemotherapies), vitamin deficiencies, and a large variety of other medical conditions). Neuropathic pain includes pain induced by expression of pathological operation of the nervous system following nerve injury due to various causes, for example, surgical operation, wound, shingles, diabetic neuropathy, amputation of legs or arms, cancer, and the like. Medical conditions associated with neuropathic pain include traumatic nerve injury, stroke, multiple sclerosis, syringomyelia, spinal cord injury, and cancer.

A pain-causing stimulus often evokes an inflammatory response which itself can contribute to an experience of pain. In some conditions pain appears to be caused by a complex mixture of nociceptive and neuropathic factors. For example, chronic pain often comprises inflammatory nociceptive pain or neuropathic pain, or a mixture of both. An initial nervous system dysfunction or injury may trigger the neural release of inflammatory mediators and subsequent neuropathic inflammation. For example, migraine headaches can represent a mixture of neuropathic and nociceptive pain. Also, myofascial pain is probably secondary to nociceptive input from the muscles, but the abnormal muscle activity may be the result of neuropathic conditions.

2) Symptoms of Pain

Symptoms of pain experienced by a patient may or may not be accompanied by signs of pain discernable to a clinician. Conversely, pain can be manifested by clinical signs without the patient being aware of symptoms.

Symptoms of pain can include a response to pain, e.g., in the form of a behavioural change. Exemplary responses to pain can include conscious avoidance of a painful stimulus, a protective response intended to protect the body or body parts from the painful stimulus, responses intended to minimize pain and promote healing, communication of pain, and physiological responses. Communicative responses can involve vocalizations of pain or modifications of facial expression or posture. Physiological responses are include responses mediated by the autonomic nervous system or endocrine system. e.g., enhanced release of adrenalin and noradrenalin, increased output of glucagon and/or hormones and/or corticosteroids. Physiological changes that can be monitored include locomotor effects such as twitching, convulsions, paralysis, dilated pupils, shivering, hyperesthesia and/or altered reflexes. Physiological cardiovascular responses to pain can include changes in blood pressure, alterations in pulse rate and quality, decreased peripheral circulation, cyanosis and congestion. Increased muscle tension (tone) is also symptomatic of pain. Changes in brain function in response to pain can be monitored by various techniques such as electroencephalography (EEG), frontal electromyography (FEMG) or positron emission tomography (PET).

Another symptom of pain can be referred pain, which is a perception of pain as being localized at a site adjacent to or at a distance from the actual site of the pain-causing stimulus. Often, referred pain arises when a nerve is compressed or damaged at or near its origin. In this circumstance, the sensation of pain will generally be felt in the territory that the nerve serves, even though the damage originates elsewhere. A common example occurs in intervertebral disc herniation, in which a nerve root arising from the spinal cord is compressed by adjacent disc material. Although pain may arise from the damaged disc itself, pain will also be felt in the region served by the compressed nerve (for example, the thigh, knee, or foot).

Nociceptive activity is a symptom of nociceptive pain. Nociceptive activity, even in the absence of consciously-perceived pain, may trigger withdrawal reflexes and a variety of autonomic responses such as pallor, diaphoresis, bradycardia, hypotension, lightheadedness, nausea and fainting.

IV. Agents

Pain-relieving agent of the invention include peptides and peptidomimetics. An exemplary agent of the invention is a chimeric polypeptide in which a tat peptide is fused at its C-terminus to NMDAR 2B 9C. Such a chimeric polypeptide has the amino acid sequence YGRKKRRQRRRKLSSIESDV (SEQ ID NO:1). Variants and mimetics of this sequence can also be used. Some variants have a flanking sequence on either end of the exemplified sequences. Flanking sequences at each end typically have fewer than 20, 10 or five amino acids. At the N-terminus, flanking residues if present can be additional residues from a HIV tat protein. Flanking sequences can also be linker amino acids of a kind typically used to join two peptide domains, e.g., Gly(Ser)$_4$ (SEQ ID NO:11), T G E K P (SEQ ID NO:12), GGRRGGGS (SEQ ID NO:13), or LRQRDGERP (SEQ ID NO:14) (see, e.g., Tang et al. (1996), J. Biol. Chem. 271, 15682-15686; Hennecke et al. (1998), Protein Eng. 11, 405-410)). For example, the number of flanking amino acids does not exceed ten. Alternatively, no flanking amino acids are present.

Other variants have deleted residues. For example, some variants have some or all of the NMDAR 2B 9C (KLSSIESDV, SEQ ID NO:3) deleted. Some variants have fewer than 2, 3, 4, 5, 6, 7, 8, 9, 10 or 11 residues of the YGRKKRRQRRRKLSSIESDV (SEQ ID NO:1) sequence deleted. Some variants have amino acid substitutions of the YGRKKRRQRRRKLSSIESDV (SEQ ID NO:1) sequence. Preferably, any substitutions are conservative substitutions, such as the replacement of an S by a T at the third position from the C-terminus. In some variants, the number of substitutions is fewer than 2, 3, 4, 5, 6, 7, 8, 9 or 10. Some variants include inserted internal amino acids. The number of such internal insertions is typically fewer than 2, 3, 4, 5, 6, 7, 8, 9, 10, 11. Preferably, positively charged residues (e.g., Y, R and K) are not substituted or deleted, or if they are substituted are replaced with other positively charged. residues. Other agents are peptidomimetics of the sequence YGRKKRRQRRRKLSSIESDV (SEQ ID NO:1) in which at least one residue is replaced with an unnatural amino acid and/or at least one bond is replaced with a nonpeptide bond. Peptidomimetics typically have a similar charge distribution and three dimensional conformation as the underlying peptide but with enhanced stability or pharmokinetics. Some agents of the invention differ from the polynucleotide YGRKKRRQRRRKLSSIESDV (SEQ ID NO:1) at fewer than 2, 3, 4, 5, 6, 7, 8, 9 or 10 sites, where a difference can be a deletion, substitution including replacement with a non, internal substitution.

Another exemplary agent of the invention is a tat peptide. A tat peptide is a fragment of a tat protein including an overrepresentation of basic residues which has capacity to facilitate uptake of linked molecule into cells or across barriers (e.g., the blood brain barrier). Tat proteins are found in HIV-1, HIV-2 and SIV viruses. Tat peptides occupy approximately, residues 35-70, 40-65, or 43-60, of a HIV-1 Tat protein. In HIV-2 and SIV, this portion of Tat generally corresponds to residues 70-100, 75-95 or 78-91, of a HIV-2 or SIV tat protein. A representative tat protein from HIV-1 is provided as GenBank I.D. 9629358 (NP 057853.1), which has the following sequence: MEPVDPRLEPWKHPGSQPKTACTNCYCKKCCFHCQVCFITKALGISYGRKKRRQRRRAH-QNSQTHQASLSKQPTSQPRGDPTGPKE (SEQ ID NO:15). The underline portion is referred to as a standard tat peptide. The standard tat peptide is a preferred agent for use in the invention.

Variants and mimetics of the tat peptide are also provided. Some agents include a tat peptide but lack other moiety independently having a pharmacologically activity (e.g., an NMDAR 2B 9C peptide) or other agent known to relieve pain. Some variants have a flanking sequence on either end of the exemplified sequences. Flanking sequences at each end typically have fewer than 20, 10 or five amino acids. Flanking residues if present can be additional residues from a HIV tat protein, such as the sequence provide above. Flanking residues can also add another functionality, such as NMDA 2B 9c or other pain relieving drug as discussed below. Flanking residues can also be linkers as discussed above. Other variants have deleted residues. Some variants have fewer than 2, 3, 4, 5, residues of the YGRKKRRQRR (SEQ ID NO:16) sequence deleted. Some variants have amino acid substitutions of the YGRKKRRQRRR (SEQ ID NO:2) sequence. Preferably, any substitutions are conservative substitutions. Optionally, the substitution preserves or increases the number of positively charged residues present. In some variants, the number of substitutions is fewer than 2, 3, 4, or 5. Some variants include inserted internal amino acids. The number of such internal insertions is typically fewer than 2, 3, 4, or 5. Preferably, positively charged residues (e.g., Y, R and K) are not substituted or deleted, or if they are substituted are replaced with other positively charged. residues. Other agents are peptidomimetics of the sequence YGRKKRRQRRR (SEQ ID NO:2) in which at least one residue is replaced with an unnatural amino acid and/or at least one bond is replaced with a nonpeptide bond. Peptidomimetics typically have a similar charge distribution and three dimensional conformation as the underlying peptide but with enhanced stability or pharmokinetics. Some agents of the invention differ from the polypeptide YGRKKRRQRRR (SEQ ID NO:2) at fewer than 2, 3, 4, sites, where a difference can be a deletion, substitution including replacement with a non, internal substitution. Some agents differ at a single site. Some variants comprise at least 7, 8, 9, 10 or 12 consecutive amino acids of a Tat protein. Some variants consists essentially of or comprises a portion of a tat protein, where at least about 60%, 70%, 80%, 90% or 100% of the amino acids are basic (e.g., histidine (H), lysine (K) or arginine (R)). Some tat peptides comprise at least 7, 8, 9, 10, 11, 12 or 13 consecutive residues of a Tat protein. Some agent comprise at least 7, 8, 9 or 10 consecutive residues of YGRKKRRQRRR (SEQ ID NO:2), e.g., YGRKK (SEQ ID NO:17). Some fragments retain a naturally-occurring tyrosine residue (Y) as the N-terminal end of the fragment.

The above agents can be screened for retention of uptake into cells, capacity to cross the blood brain barrier, capacity to inhibit N-type calcium channels, and/or capacity to inhibit pain in an animal models. Examples of such screens are described below. Preferred agents have at least capacity to be taken up into cells and capacity to inhibit pain in animal models. Some agents also have capacity to inhibit N-type calcium channels and/or capacity to cross the blood brain barrier.

Peptides such as those just described can optionally be derivatized (e.g., acetylated, phosphorylated and/or glycosylated) to improve the binding affinity of the inhibitor, to improve the ability of the inhibitor to be transported across a cell membrane or to improve stability. As a specific example, for inhibitors in which the third residue from the C-terminus is S or T, this residue can be phosphorylated before use of the peptide.

Peptides of the invention can be synthesized by solid phase synthesis or recombinant methods. Peptidomimetics can be synthesized using a variety of procedures and methodologies described in the scientific and patent literature, e.g., Organic Syntheses Collective Volumes, Gilman et al. (Eds) John Wiley & Sons, Inc., NY, al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymol. 267:220-234.

An agent of the invention can be attached to a second therapeutic agent or moiety such as a therapeutic agent, a label, or a second internalization agent. Examples of other agents for use in combined methods of therapy are described below. Examples of internalization agents other than tat include antennapedia internalization peptide SGRQIKIW-FQNRRMKWKKC (SEQ ID NO:18) (Bonfanti, Cancer Res. 57, 1442-6 (1997)) (and variants thereof), Penetratin, SynB1 and 3, Transportan, Amphipathic, HSV VP22, gp41NLS, polyArg, and others described in the following references (Temsamani, Drug Discovery Today, 9(23):1012-1019, 2004; De Coupade, Biochem J., 390:407-418, 2005; Saalik Bioconjugate Chem. 15: 1246-1253, 2004; Zhao, Medicinal Research Reviews 24(1):1-12, 2004; Deshayes, Cellular and Molecular Life Sciences 62:1839-49, 2005) (all incorporated by reference).

Coupling of two or more agents can be accomplished in the form of a fusion protein or via a coupling or conjugating agent. Numerous such agents are commercially available and are reviewed by S. S. Wong, Chemistry of Protein Conjugation and Cross-Linking, CRC Press (1991). Some examples of cross-linking reagents include J-succinimidyl 3-(2-pyridyldithio) propionate (SPDP) or N,N'-(1,3-phenylene) bis-maleimide; N,N'-ethylene-bis-(iodoacetamide) or other such reagent having 6 to 11 carbon methylene bridges (which relatively specific for sulfhydryl groups); and 1,5-difluoro-2, 4-dinitrobenzene (which forms irreversible linkages with amino and tyrosine groups). Other cross-linking reagents include p,p'-difluoro-m,m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Optionally, the pain-relieving agent (e.g., a tat peptide) is not attached or conjugated to another pain-relieving agent or another therapeutic agent. Optionally the pain-relieving agent is conjugated to another therapeutic agent that is not a pain-relieving agent. The agent (e.g., a tat peptide) is optionally coadministered with a second agent that is not conjugated or attached to it. The agents can be coadministered at the same time or at different times, e.g., within an hour or a day or a week of each other. The agents can be co-administered together in a single formulation or in separate formulations. Alternatively, the pain-relieving agent is not co-administered in combination with another pain-relieving agent or another therapeutic agent.

V. Patients to be Treated

An agent of the invention can be administered to any individual having or a risk of having pain as described above, and/or one or more symptoms of pain, as described above. The individual is preferably a mammal such as a humans. Mammals other than humans include primates (e.g., monkey) or rodents (e.g., mouse or rat).

The methods can be used for treatment or prophylaxis of pain in patients with or without concurrent diseases or disease susceptibilities. In some methods, the patient is not suffering from an excitotoxicity-caused condition or has not suffered from an excitotoxicity-caused condition recently (e.g., in the last hour, day, week, month or year). In some methods, the patient is known or suspected of having an excitotoxicity-caused condition but is not known or suspected to be suffering from an episode of excitotoxicity, or to have had an episode of excitotoxicity recently (e.g., in the last hour, day, week, month or year). In some methods, the patient is known to have to have had an excitotoxicity-caused condition but is not believed to be currently experiencing neuronal degeneration or damage that results from excitotoxicity.

In some methods, the patient is free of excitotoxicity-caused condition is caused by excitotoxicity mediated by glutamate receptors, such as NMDA receptor-mediated excitotoxic injury. Such conditions include spinal cord injury, stroke, traumatic brain injury and neurodegenerative diseases of the central nervous system (CNS) such as multiple sclerosis, Alzheimer's disease, Amyotrophic lateral sclerosis (ALS), Parkinson's disease, alcoholism and Huntington's disease.

In some methods, the patient is free of known excitotoxicity-mediated damage of neurons. In other methods, the patient is not suffering from pain due to a disease or disorder, e.g., the patient is experiencing pain due to a traumatic injury. In other situations, the patient is free of another medical condition that is painless or does not cause significant pain.

VI. Methods of Treatment

Agents of the invention are administered to patients having or at risk of pain. Treatment refers to the administration of an agent resulting in an alleviation, decrease, delay, inhibition and/or prevention of pain or at least one sign or symptom of pain. Treatment includes a decrease in intensity and/or duration of any sign or symptom of pain, even if other sign or symptoms are unchanged or even increased by the treatment.

In prophylactic applications of treatment, at least one agent is administered to a patient at enhanced risk of developing pain or an increase in at least one symptom of pain relative to the general population. Such patients include patients known to be at high risk of pain, e.g., patients about to undergo surgery or suffering from diseases associated with severe or chronic pain, such as diabetes and cancer. The agent can be administered before an onset or increase or exacerbation of pain, in an amount sufficient to eliminate, or reduce the risk of, or delay the onset of, pain. In therapeutic applications, at least one agent is administered to a patient suspected of, or already suffering from pain. The agent for example is administered in an amount sufficient to abolish, or at least lessen, at least one symptom of the pain and its complications.

The methods of the invention can be used to treat or effect prophylaxis of any kind of pain, including those just described and any combination thereof. Some methods are used to treat or effect prophylaxis of neuropathic pain, including central or peripheral or both. Some methods are used to treat or chronic pain, e.g., pain lasting more than 1, 3, 6 or 12 months. Some methods are used to treat severe chronic pain.

In therapeutic treatment, treatment is optionally initiated as soon as possible after the onset of pain. Multiple doses can be administered at intervals of 1, 2, 3, 4, 8, 16, 24 hrs or greater. Dosing can also be daily or weekly, or at irregular intervals responding to exacerbations of pain intensity. Administration can also be on a continuous basis, such as by infusion.

In patients undergoing treatment for pain who have a concurrent disease associated with excitotoxicity, the agent can be administered to alleviate pain at a timepoint outside the therapeutic time window for treatment of excitotoxic neurodegeneration for that agent. For example, the agent is administered to treat pain after about 4, 5, 6, 8, 12, 18, 24, 48 or 120 hours after an excitotoxic insult.

The response of the patient to the administration of an agent, e.g., a peptide or peptidomimetic of the invention, can be monitored by determining the effect of the agent on pain.

1) Combination Therapy

An agent of the invention can be administered in combination with a conventional agent for treating pain, and/or for underlying disease associated with pain. The two agents can be administered separately at the same or different times. Alternatively, the two agents can be attached to each other to form a bifunctional agent.

A) Combinations of Agents

Some examples of analgesic agents that can be administered with agent of the invention include conotoxins and Symlin. Conotoxins include α-conotoxin which inhibits acetylcholine receptors at nerves and muscles; δ-conotoxin which inhibits the inactivation of voltage-dependent sodium channels; κ-conotoxin which inhibits potassium channels, μ-conotoxin which inhibits voltage-dependent sodium channels in muscles, or preferably ω-conotoxin which inhibits N-type voltage-dependent calcium channels (Prialt), and synthetic derivatives of the naturally-occurring peptides. Preferred conotoxins include ω-conotoxin-GVIA, ω-conotoxin-MVIIA (also called SNX-111, Ziconotide and Prialt), AM336 (ω-conotoxin-CVID), which has a better therapeutic index than Prialt, and huwentoxin-I. Other useful analgesic agents include peptide ligands or active fragments or derivatives thereof that can bind to various receptors related to pain. Examples include α-endorphin, endomorphin-1, endomorphin-2, dermorphin, β-casomorphin (bovine or human), Morphiceptin, Leu-enkephalin, Met-enkephalin, DALDA, and PL107, substance P, tachykinins, neurokinins, prostaglandins, bradykinin, serotonin, neurotrophins, chemokines, botulinum toxin, prokineticin and NK1 receptor antagonists; some of which described in US 2006-0105947 and U.S. Pat. No. 6,759,520, incorporated by reference in its entirety.

Examples of small molecule analgesics that can be administered with agents of the invention include NSAIDs, COX 2 inhibitors, COX-3 inhibitors, iNOS inhibitors, PAR2 receptor antagonists, neuroleptic agents, opioids, N-acetylcholine receptor agonists, glycine antagonists, vanilloid receptor antagonists, neurokinin antagonists calcitonin gene-related peptide antagonists and cyclooxygenase (COX)-inhibiting nitric oxide donators (CINOD)s. Other pain relieving drugs include codeine, vicodin, morphine, Demerol, percocet, Darvon and Darvocet.

Other pain relieving drugs target any of the following ion channels or receptors calcium channels (e.g., L-type and/or N-type), the acid-sensing ion channel family (ASIC) (Waldmann et al., 1997); ATP-sensing ion channels of the P2X family (Chen et al., 1995; Lewis et al., 1995; Chessel et al., 2005); nociceptor-specific TTX-insensitive Na channels (Nav1.8 and Nav1.9) (Akopian et al., 1996; Dib-Hajj et al., 2002), vanilloid receptors such as TRPV1, nicotinic acetylcholine receptors, opioid receptors (e.g., μ, δ, or κ) receptors), opioid-like receptors (e.g., ORL-1), the NK1 receptor though which substance P acts, and other receptors for extracellular pain mediators such as prostaglandins, bradykinin, serotonin, adenosine, neurotrophins, ATP, proteinases, chemokine, and prokineticin, the activation of which can elicit peripheral nociceptor sensitization.

B) Combination Therapy for Diseases Associated with Pain

Agents of the invention (e.g., a tat peptide) can also be administered in combination with a therapeutic agent used to treat a disease associated with pain. The therapeutic agent and the analgesic agent can be administered as separate drugs or attached together, e.g., as a fusion protein. Examples of therapeutic agents that can be used in such combination therapy include Lupron, insulin, oxytocin, exendin-4, parathyroid hormone, calcitonin, Fuzeon, Integrilin, DDAVP, Sandostatin, or Symlin, or active fragments or derivatives thereof.

A wide variety of diseases can involve pain. For example, diseases that can result in chronic pain include diabetes, arthritis (e.g., osteoarthritis, rheumatoid Arthritis and juvenile chronic arthritis), cancer or the toxic effects of chemotherapy, fibromyalgia, shingles, irritable bowel syndrome, blood vessel problems or sickle-cell disease.

Diseases associated with episodic general pain include polymyalgia rheumatica, hypochondria, depression, diabetes, pernicious anemia, sickle cell disease, and syphilis. Diseases associated with neuropathic pain include neuralgia (e.g., trigeminal neuralgia, atypical facial pain, and postherpetic neuralgia caused by shingles or herpes), peripheral neuropathies, Charcot-Marie-Tooth disease, Friedreich's ataxia, diabetes (e.g., diabetic neuropathy), dietary deficiencies (especially vitamin B-12), excessive alcohol use (alcoholic neuropathy), uremia (from kidney failure), cancer, AIDS, Hepatitis, Colorado tick fever, diphtheria, Guillain-Barre syndrome, HIV infection without development of AIDS, leprosy, Lyme, polyarteritis nodosa, rheumatoid arthritis, sarcoidosis, Sjogren syndrome, syphilis, systemic lupus erythematosus, and exposure to toxic compounds.

Diseases that involve inflammatory pain include: (A) Arthritic disorders, e.g., a rheumatoid arthritis; a juvenile rheumatoid arthritis; a systemic lupus erythematosus (SLE); a gouty arthritis; a scleroderma; an osteoarthritis; a psoriatic arthritis; an ankylosing spondylitis; a Reiter's syndrome (reactive arthritis); an adult Still's disease; an arthritis from a viral infection; an arthritis from a bacterial infection, such as, e.g., a gonococcal arthritis and a nongonococcal bacterial arthritis (septic arthritis); a Tertiary Lyme disease; a tuberculous arthritis; and an arthritis from a fungal infection such as a blastomycosis; (B) Autoimmune diseases, e.g., a Guillain-Barre syndrome, a Hashimoto's thyroiditis, a pernicious anemia, an Addison's disease, a type I diabetes, a systemic lupus erythematosus, a dermatomyositis, a Sjogren's syndrome, a lupus erythematosus, a multiple sclerosis, a myasthenia gravis, a Reiter's syndrome and a Grave's disease. (C) Connective tissue disorders, e.g., a spondylarthritis a dermatomyositis, and a fibromyalgia; (D). Injury—caused inflammation; (E) Infection, e.g., a tuberculosis or an interstitial keratitis; (F) Neuritis, e.g., Brachial neuritis, retrobulbar neuropathy, optic neuropathy and vestibular neuritis; and (G) Joint inflammation, e.g., bursitis or tendonitis. Types of headache pain (cephalgia) include muscular/myogenic, vascular, traction or inflammatory, cluster, hormone, rebound or chronic sinusitis headaches.

Somatic pain can be associated with excessive muscle tension, repetitive motion disorders, muscle disorders such as a polymyositis, a dermatomyositis, a lupus, a fibromyalgia, a polymyalgia rheumatica, and a rhabdomyolysis, myalgia, an infection such as an abscess in the muscle, a trichinosis, an influenza, a Lyme disease, a malaria, a Rocky Mountain spotted fever, Avian influenza, the common cold, community-acquired pneumonia, meningitis, monkeypox, Severe Acute Respiratory Syndrome, toxic shock syndrome, trichinosis, typhoid fever, and upper respiratory tract infection. Visceral pain can be associated with diseases such as irritable bowel syndrome, a chronic functional abdominal pain (CFAP), a functional constipation, a functional dyspepsia, a non-cardiac chest pain (NCCP) and a chronic abdominal pain, chronic gastrointestinal inflammation, e.g., a gastritis, an inflammatory bowel disease, like, e.g., a Crohn's disease, an ulcerative colitis, a microscopic colitis, a diverticulitis and a gastroenteritis; an interstitial cystitis; an intestinal ischemia; a cholecystitis; an appendicitis; a gastroesophageal reflux; an ulcer, a nephrolithiasis, an urinary tract infection, a pancreatitis and a hernia.

Many diseases associated with chronic pain are disclosed in the PCT publication WO 07/138,336, incorporated by reference in its entirety.

VII. Pharmaceutical Compositions, Dosages and Routes of Administration

The agents of the invention can be administered in the form of a pharmaceutical composition. Pharmaceutical compositions are usually manufactured under GMP conditions. Pharmaceutical compositions can be provided in unit dosage form (i.e., the dosage for a single administration) containing any of the dosages indicated above. Pharmaceutical compositions can be manufactured by means of conventional mixing, dissolving, granulating, dragee-making, levigating, emulsifying, encapsulating, entrapping or lyophilizing processes. In particularly, lyophilized agents of the invention can be used in the formulations and compositions described below.

Pharmaceutical compositions can be formulated in conventional manner using one or more physiologically acceptable carriers, diluents, excipients or auxiliaries that facilitate processing of agents into preparations which can be used pharmaceutically. Proper formulation is dependent on the route of administration chosen.

Administration can be parenteral, intravenous, oral, subcutaneous, intraarterial, intracranial, intrathecal, intraperitoneal, topical, intranasal or intramuscular. Intravenous administration is preferred.

An agent of the invention can be administered locally or topically to that area, e.g., via intramuscular injection, if so desired (e.g., the pain is localized to a particular part of the body). The agent can optionally be administered to the CNS, e.g., intravenously or intrathecally, such as when the pain is systemic or involves the CNS tissues. The agent can also be administered in a manner that allows the agent to contact the peripheral nerve system (e.g., dorsal root ganglions).

Pharmaceutical compositions for parenteral administration are preferably sterile and substantially isotonic. For injection, agents can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents.

Alternatively the agent can be in powder form for constitution with a suitable vehicle, e.g., sterile pyrogen-free water, before use.

For transmucosal administration, penetrants appropriate to the barrier to be permeated are used in the formulation. This route of administration can be used to deliver the compounds to the nasal cavity or for sublingual administration.

For oral administration, the agent can be formulated with pharmaceutically acceptable carriers as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents can be added, such as the cross-linked polyvinylpyrrolidone, agar, or alginic acid or a salt thereof such as sodium alginate. If desired, solid dosage forms can be sugar-coated or enteric-coated using standard techniques. For oral liquid preparations such as, for example, suspensions, elixirs and solutions, suitable carriers, excipients or diluents include water, glycols, oils, alcohols. Additionally, flavoring agents, preservatives, coloring agents and the like can be added.

In addition to the formulations described previously, the agents can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems can be employed. Liposomes and emulsions can be used to deliver agents. Certain organic solvents such as dimethylsulfoxide also can be employed, although usually at the cost of greater toxicity. Additionally, the compounds can be delivered using a sustained-release system, such as semipermeable matrices of solid polymers containing the therapeutic agent.

Sustained-release capsules can, depending on their chemical nature, release the agents for a few weeks up to over 100 days. Depending on the chemical nature and the biological stability of the therapeutic reagent, additional strategies for protein stabilization can be employed.

If the agents of the invention contain charged side chains or termini, they can be included in any of the above-described formulations as the free acids or bases or as pharmaceutically acceptable salts. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms.

The agents of the invention are used in an amount effective to achieve the intended purpose. A therapeutically effective amount means an amount of agent sufficient to eliminate, reduce or inhibit worsening of at least one sign and/or symptom of pain in patient presently experiencing signs and/or symptoms of pain. For example, an amount is considered therapeutically effective if it significantly reduces at least one sign or symptom of pain in a population of treated patients (human or animal) compared with a control population of untreated patients. The amount is also considered therapeutically effective if an individual treated patient achieves an outcome more favorable than the mean outcome in a control population of comparable patients not treated by methods of the invention. A prophylactically effective amount of an agent means an amount of agent sufficient to delay, inhibit or prevent development of at least one sign or symptom of pain in a patient not currently experiencing signs and/or symptoms but who is considered at heightened risk relative to the general population of developing such signs/ and/o symptoms. For example, an amount is considered to be prophylactically effective if a population of patients at risk of developing symptoms of pain treated with the agent develops reduced signs or symptoms relative to a control population not treated with the agent. Reference to an effective amount means either a therapeutically or prophylactically effective amount. Reference to an effective regime means a combination of an effective amount and dosing frequency required to achieve the intended purpose as described above.

Assuming an average body weight of 75 kg, suitable doses in humans are usually less than 300 µmoles, for example less than 30 µmoles. Dosages sometimes range from 0.03 nmoles to 30 µmoles, e.g., 0.03 nmoles to 3 µmoles, or 0.3 nmoles to 600 µmoles, or 3 nmoles to 60 µmoles, or 30 nmoles to 30 µmoles. Some dosage ranges include a total dose of 0.05 to 500 nanomoles agent per patient with a body weight of 75 kg, optionally 0.5 to 50 nanomoles per patient, e.g., about 0.5, 1, 2, 5, 10, 20 or 50 nanomoles per 75 kg patient. In some methods, the total dosage is 1-10 nanomoles, e.g., about 1, 5 or 10 nanomoles per 75 kg patient. In some situations, the dose can be 0.1 to 1 nanomoles, e.g., 0.1, 0.2, 0.5 or 0.8 nanomoles per 75 kg patient. In other situations, the dose can be 10-100 nanomoles, e.g., 20, 50, 80 or 100 nanomoles per 75 kg patient. Optionally, the dose is less than 2250 nanomoles per 75 kg patient. Optionally, the dose is less than 75 nanomoles per 75 kg patient. Dosage can be adjusted to account for variation in body weight. The above doses can be converted to nanomoles of agent per kg body weight by dividing, for example by 75 kg.

Dosages can be converted from units of moles to grams by multiplying by the molar weight of a of agent (e.g., 2519 for Tat-NR2B9c). Suitable dosages of therapeutic agent for use in humans are usually less than 10 mg/kg, e.g., less than 1 mg/kg. Dosages sometimes range from $10^{-4}$ to 1 mg/kg, $10^{-4}$ to 0.1 mg/kg, $10^{-4}$ to 20 µg/kg or $10^{-3}$ to 2 µg/kg or $10^{-2}$ to 2 µg/kg, e.g., 50, 100, 150, 200, 500, 1000 or 1500 ng/kg. Some dosage ranges include a dose of 10-200 ng of agent per kg body weight, such as about 1, 5, 10, 20, 50, 80, 120, 160 or 200 ng/kg per patient. In some methods, the dosage is 2-20 µg/kg, e.g., 2, 4, 6, 8, 10, 12, 16, 18, or 20 µg/kg. Optionally the dose is less than 75 µg/kg. Optionally the dose is less than 2.5 µg/kg. Total dosages per patient can be calculated by multiplying the dose per kg body weight by the patient's weight in kg. For example, the total dose for a 75 kg patient can be calculated by multiplying the above doses by 75.

Dosages can also be expressed in desired pharmacokinetic parameters, such as $C_{max}$ (i.e., The maximum or "peak" concentration in the blood of a drug observed after its administration), $C_{average}$ (average steady-state concentration in blood) and AUC (i.e., the area under the plasma, e.g., serum or blood, concentration versus time curve) equivalent to a stated regime of dose, frequency and route of administration.

The amount of agent to be administered depends on the patient being treated, on the patient's weight, the severity of the affliction, the manner of administration and the judgment of the prescribing physician. The therapy can be repeated intermittently while symptoms detectable or even when they are not detectable. The therapy can be provided alone or in combination with other drugs.

Therapeutically effective dose of the present agents can provide therapeutic benefit without causing substantial toxicity. Toxicity of the agents can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Agents, e.g., peptides or peptidomimetics, exhibiting high therapeutic indices are preferred (see, e.g., Fingl et al., 1975, In: *The Pharmacological Basis of Therapeutics*, Ch. 1, p. 1).

VIII. Calcium Channels

As discussed above, one mechanism that may contribute at least in part to the efficacy of the agents in treatment of pain involves binding to N-type calcium channels, particularly the neural N-type channel that is blocked by ω-conotoxinGVIA. Optionally, the agent binds to the $α_1$ subunit of the VDCC.

N-type calcium channels are located on presynaptic nerve terminals regulate neurotransmitter release, including that from the spinal terminations of primary afferent nociceptors. The pharmacological effects of binding to N-type channels have been well characterized in connection with the drug Ziconotide (or Prialt, a synthetic form of the cone snail peptide omega-conotoxin M-VII-A precursor). Binding to N-type calcium channels has been associated with numerous activities, including analgesia much stronger than that induced by morphine.

N-type calcium channels are hetero-oligomeric complexes consisting of $\alpha_{1B}$-(Cav2.2), $\beta$-, and $\alpha_2\delta$-subunits and sometimes $\gamma$ subunits. The $\alpha_{1B}$-subunit forms the main channel and is encoded by a single gene. There are four $\alpha_2\delta$-subunit genes ($\alpha_2\delta$-$\alpha_2\delta$-4)(Snutch et al., Molecular properties of voltage-gated calcium channels. In: Voltage-gated calcium (Zamponi G, ed), pp 61-94. New York: Landes Bioscience, 2005. Catterall, Biochemical studies of $Ca^{2+}$ channels. In: Voltage-Gated Calcium (Zamponi G, ed), pp 48-60. New York: Landes Bioscience, 2005). There is close conservation of N-type calcium channels across species.

The $\alpha_{1B}$-subunit N-type calcium channel described by Williams et al., 1992 (Science 257 (5068), 389-395 (1992), Genebank Acc No. Q00975, Species: *Homo Sapiens*) and Coppola et al., 1994 (FEBS Lett. 338 (1), 1-5 (1994), Genebank Acc No 055017, Species: *Mus Musculus*) and Dubel et al., 1992 (Proc. Natl. Acad. Sci. U.S.A. 89 (11), 5058-5062 (1992) Genebank Acc No Q02294, Species: *Rattus norvegicus*) including splice variants and fragments thereof having similar calcium channel activity to the intact protein is preferred for screening. Allelic variants and splice variants having at least 90% sequence identity with any of the above sequences can also be used in screening methods of the invention. Optionally, the am subunit can be used in combination with an alpha2(a-e)/delta, beta1-4, and/or gamma subunit.

Screening Methods and Assays

Desired activity of agents of the invention can be tested or confirmed by several assays. Parallel assays are usually performed on an agent versus a control, and a desired activity is seen from detectable and preferably statistically significant difference (e.g., greater binding, greater cellular uptake, greater pain reduction or inhibition relative to the control).

1. Measuring Binding to Target (e.g., Calcium Channels)

Agents can be screened for binding to a target of interest (e.g., N-type calcium channels) by a competitive binding assay using a labeled peptide known to bind such channels (e.g., Ziconotide). The N-type calcium channel can be provided in purified form or naturally or recombinantly expressed from cells. If provided in purified form, the N-type calcium channel can optionally be immobilized to beads or to a microtiter well. The amount of label bound to the calcium channel after incubation with the labeled peptide and test agent is inversely related to the capacity of the test agent to bind to the calcium channel. The assay can be performed on a high throughput basis in the wells of a microtiter plate. Negative and positive controls can also be included. A negative control can be vehicle. A positive control can be unlabelled form of the peptide known to bind N-type calcium channels.

2. Measuring Inhibition of Targets In Vitro

Agents can be screened for their capacity to inhibit activity of the target, e.g., inhibition of ionic currents mediated by N-type calcium channels Inhibition means a statistically significant reduction in the measured ionic current carried by calcium channels. Such a reduction should be greater than a 20% reduction in measured current, preferably greater than 30% reduction, and more preferably greater than 40% reduction Inhibition can be determined by, e.g., performing whole-cell patch clamp recordings in dorsal root ganglion neurons, in which calcium currents are expressed. Cultures of dorsal root ganglions (DRGs) can be prepared from Swiss mice at 13-14 days of gestation. In brief, DRG's are dissected and subjected to trypsin digestion for 20 min at 37° C., mechanically dissociated and plated on cover slips coated with poly-D-lysine. They are grown in serum free MEM (Neurobasal MEM, B-27-Gibco Invitrogen Corporation, Carlsbad, Calif.). After 3-5 days, 10 µM FUDR solution is added to inhibit glial proliferation. The cultures are maintained at 37° C. in a humidified 5% $CO_2$ atmosphere and fed twice a week. Whole-cell recording is carried out at room temperature 10-14 days after plating. Electrophysiology recordings: Whole-cell recordings are performed with an Axopatch-1B amplifier (Axon Instruments, Foster City, Calif.) in the voltage-clamp mode. Recording electrodes, with resistances of 3-5 M$\Omega$, are constructed from thin-walled borosilicate glass (1.5 mm diameter; World Precision Instruments, Sarasota, Fla.) using a two-stage puller (PP83; Narishige, Tokyo, Japan). Data are digitized, filtered (2 kHz), and acquired on-line using the programs of pClamp 9 (Axon Instruments). The pipettes are filled with a solution containing (mM): CsCl 110, MgCl2 3, EGTA 10, HEPES 10, MgATP 3, GTP 0.6. The pH is adjusted to 7.2 with CsOH. The bath solution contained (mM): CaCl2 1, BaCl2 10, HEPES 10, TEA-Cl 160, Glucose 10, TTX 0.0002 at pH (NaOH) 7.4. Whole-cell currents are elicited using 40 ms depolarizing pulses to +20 mV from a holding potential of −60 mV, applied every 15 s. To test the use-dependent inhibition, currents are elicited using 10 ms depolarizing pulses to +20 mV from a holding potential of −60 mV, applied every 0.02 s (50 Hz), 0.05 s (20 Hz), 0.1 s (10 Hz) or 15 s (0.07 Hz) respectively. The identity of a target that is inhibited by a test agent can be identified by checking for further inhibition using specific inhibitors of that target, as described in the Examples.

3. Assessment of Analgesic Activity In Vivo

Agents can be screened for prophylaxis or alleviation of pain in animals. Humans are a preferred type of mammal. Mammals other than humans can also be used, such as primates (e.g., monkey) or rodents (e.g., mouse or rat).

Nociceptive tests in mammals (e.g., rodents) for pain include the tail-flick (a spinally-mediated nociceptive reflex) test (D'Amour et al. (1941), J. Pharmacol. Exp. Ther. 72: 74-79), the hot-plate test, the Randall-Selitto test (Swingle et al. (1971), Proc. Soc. exp. Biol. Med. 137: 536-538) and the tail-pinch test. Sucs tests can be used to evaluate the nociceptive threshold to different kinds of noxious stimuli such as threshold to heat (the tail-flick test, the hot-plate test, the Hargreaves' test of paw withdrawal, and by brief immersion of the tail or hindpaw into hot water); or tactile threshold to punctuate stimuli e.g., by the Von Frey test for allodynia test, J Neurosci Methods. 1999 Mar. 1; 87(2):185-93. Dynamic allodynia can be assessed by lightly stroking the planter surface of the hind paw with a cotton bud, where dynamic allodynia is considered to be present if animals respond to the cotton stimulus within 8 sec of commencing stroking Pain response to noxious chemical agents can be measured e.g., by monitoring abdominal writhing after intraperitoneal injection of dilute acetic acid, and the aversive drinking test by adding capsaicin to drinking water (which can be used to evaluate trigeminal nociception).

Tests for inflammatory pain include the formalin paw test (Tjolsen et al. (1992), Pain 51: 5-17), the, test for formalin-induced facial pain (Clavelou et al. (1989), Neurosci. Lett. 103: 349-353), and paw tests upon administration of substances such as carageenan, capsaicin or bradykinin. Arthritic conditions can be simulated by various models, including injection of agents such as carageenan, uric acid or mustard oil or adjuvant into various joints. Visceral pain can be modeled by intraperitoneal injection of substances such as bradykinin, acetylcholine, acetic acid or phenylquinone. The streptozocin (STZ)-induced diabetes neuroropathy model induces a reproducible mechanical allodynia within 3 weeks (Chen and Pan, J Neurophysiol 87: 2726-2733, 2002).

Tests for neuropathic pain resulting from peripheral nerve injury include chronic constriction injury (e.g., Bennet and Xie model of sciatic nerve ligation, Pain 33: 87-107); partial nerve ligation (Seltzer et al., 1990), spinal nerve transaction or ligation (Lombard et al., 1979; Kim & Chung, 1992), cryoneurolysis (deleo et al., 1994) sciatic nerve ischemia (Kupers et al., 1998). A common test is the tactile allodynia test (Chaplan et al. (1994) J. Neurosci. Meth. 53: 55-63). Taxol induced neuropathic pain does not contain an inflammatory component. Models that are specific for certain peripheral neuropathic conditions include animal models of trigeminal nerve neuralgia (Vos and Maciewicz, 1994), diabetic neuropathy (Burchiel et al., 1985), and vincristine neuropathy (Aley et al., 1996). The neuroma model (Wall et al., 1979) can reflect phantom pain resulting from limb amputation.

Animal models of pain resulting from spinal cord injury include cord transaction or partial transaction (Levitt & Levitt, 1981), an irradiation-induced ischemia model (Hao et al. 1991), an excitotoxic model using intraspinal injection of quisqualate (Yezeierski & Park, 1993) and a contusion model (Siddall et al., 1995).

In humans, pain and the effect of test agents upon pain can be evaluated using a variety of tests. Any one or more symptoms of pain, including those discussed above, can be evaluated before and after administration. Any significant reduction in one or more symptoms after administration indicates that the agent is therapeutically effective. Numerous pain questionnaires and scales have been designed to evaluate a patient's pain, using different methods. Pain may be evaluated as a single measure (intensity only) or using several measures (duration and intensity).

A list of pain ranking systems can be found in Appendix 35 of the Draft Report on Pain Assessment project for the 'Do Once and Share' (DOaS) programme by the U.K. National Library for Health, incorporated by reference in its entirety. Useful pain scales include: the Visual Analog Scale, McGill Pain Questionnaire, and the Descriptor differential scale. Such pain ranking systems and scales have been described in the following references, each incorporated by reference in its entirety: "Measurement of pain". J. Rheumatol. 9 (5): 768-9. PMID 6184474. Melzack R (September 1975). "The McGill Pain Questionnaire: major properties and scoring methods". Pain 1 (3): 277-99. PMID 1235985. Gracely R H, Kwilosz D M (December 1988). "The Descriptor Differential Scale: applying psychophysical principles to clinical pain assessment". Pain 35 (3): 279-88. PMID 3226757; "The subjective experience of acute pain. An assessment of the utility of 10 indices". Clin J Pain 5 (2): 153-9. PMID 2520397. Hartrick C T, Kovan J P, Shapiro S (December 2003) (incomplete citation?).

A patient's sensitivity to pain (pain threshold) can also be measured using a dolorimeter. Useful dolorimeters include a sonic palpometer, a pressure-controlled palpometer, laser-based d Dolorimeter Analgesia meter (IITC Life Sciences), Baseline Algorimeter (Kom Kare Company), Björnstrom's algesimeter which measures sensitivity of the skin to pain; or Boas' algesimeter which measures sensitivity over the epigastrium.

4. Measuring Internalization of Agents

An agent can be tested for internalization or transport activity in an animal. The agent (such as a tat peptide) can for example be labeled and injected into an animal, such as a mouse. Intraperitoneal or intravenous injection is suitable, for example. About an hour after injection, the mice are sacrificed, perfused with fixative solution (3% paraformaldehyde, 0.25% glutaraldehyde, 10% sucrose, 10 U/mL heparin in saline). Brains are then removed, frozen and sectioned. Sections are analyzed for fluorescence using a confocal microscope. Internalization activity is determined from fluorescence, optionally relative to positive and negative controls. A suitable positive control is an agent comprising standard tat peptide sequence. A suitable negative control is fluorescently labeled active agent lacking the tat sequence. Unlabelled vehicle can also be used as a negative control.

Similar experiments can be performed in cell culture to test tat variants (see US20030050243). A variant fluorescently labeled tat peptide, optionally linked to an active peptide is applied to a cortical neuronal culture. Uptake is determined using fluorescence microscopy over several minutes after application. Increased uptake can be determined relative to positive and negative controls as described for the experiments on uptake in an animal.

EXAMPLES

Example 1

Screening for Side Effects of Tat-NR2B9c

Tat-NR2B9c is a chimeric peptide of a standard tat peptide and KLSSIESDV (SEQ ID NO:3) previously shown to be effective in a rat model of stroke. This example screens the peptide Tat-NR2B9c for capacity to inhibit binding of known ligands to various receptor proteins. Examples of receptors screened included N-type calcium channels.

The screen was performed as a competitive binding assay in which unlabelled Tat-NR2B9c at a concentration of 10 μM competed with an I125 labeled ligand for binding to its receptor in the presence of unlabeled ligand to increase sensitivity. At 10 μM, Tat-NR2B9c showed 100% inhibition of radiolabeled ω-Conotoxin GVIA binding to N-type Ca channels. Tat-NR2B9c also showed 80% inhibition of IL-8/IL-8RB at the same concentration.

Example 2

Mutagenesis of a Standard Tat Peptide

The sequence of the standard tat peptide and the potent analgesic drug

```
                                        (SEQ ID NO: 1)
   YGRKKRRQRRRKLSSIESDV                 (Tat-NR2B9c)

(SEQ ID NO: 19)
   CKGKGAKCSRLMYDCCTGSCRSGKCG           (Ziconotide)
```

Variants of Tat-NR2B9c were tested for inhibition of N-type calcium channels. These variants included a variant in which the Y residue at position 1 of Tat-NR2B9c was mutated to F, and variants with modifications of a stretch of basic residues in Tat-NR2B9c. The peptides were each applied at 100 μM. The following peptides were tested (the $Ca^{2+}$ current in shown as a percentage after each peptide): 1990 TAT: YGRKKRRQRRR (SEQ ID NO:2) (57+/−1.6% (n=5)); 1991 2B9c: KLSSIESDV (SEQ ID NO:3) (94+/−1.7% (n=5)); 1992 Tat-NR2B9c-AA; YGRKKRRQRRRKLSSIEADA (SEQ ID NO:4) (74+/−2.4% (n=6)); 1993 F-Tat-NR2B9c: FGRKKRRQRRRKLSSIESDV (SEQ ID NO:5) (91+/−1.6% (n=5)); 1994 Tat-NR2B9c K to A: YGRKKRRQRRR ALSSIESDV (SEQ ID NO:6) (77+/−1.8% (n=7)); 1995

F-Tat-NR2B9c K to A: FGRKKRRQRRRALSSIESDV (SEQ ID NO:7) (97+/−0.2% (n=6)); 1976: YGRKKRRQR-RRKLSSIESDX (SEQ ID NO:9) where X=norvaline (66+/−3.4% (n=6)); 1977: YGRKKRRQRRRKLSSIESDX (SEQ ID NO:10) where X=L-t-butyl-glycine (65+/−5.1% (n=5)); 1987: D-isomer of Tat-NR2B9c (82+/−2.2% (n=6)). Tat-NR2B9c (68+/−1.7% (n=7)). Data were plotted as mean+/−s.e.m.

The peptides were also tested in the following patch clamp assay. Peptides were screened for their capacity to inhibit ionic currents mediated by N-type calcium channels using whole-cell patch clamp recordings in dorsal root ganglion neurons, in which N-type calcium currents are expressed. Cultures of dorsal root ganglions (DRGs) were prepared from Swiss mice at 13-14 d of gestation. In brief, DRG's were dissected and subjected to trypsin digestion for 20 min at 37° C., mechanically dissociated and plated on cover slips coated with poly-D-lysine. They were grown in serum free MEM (Neurobasal MEM, B-27-Gibco Invitrogen Corporation, Carlsbad, Calif.). After 3-5 days, 10 µM FUDR solution was added to inhibit glial proliferation. The cultures were maintained at 37° C. in a humidified 5% $CO_2$ atmosphere and were fed twice a week. Whole-cell recording were carried out at room temperature 10-14 days after plating. Electrophysiology recordings: Whole-cell recordings were performed with an Axopatch-1B amplifier (Axon Instruments, Foster City, Calif.) in the voltage-clamp mode. Recording electrodes, with resistances of 3-5 MΩ, were constructed from thin-walled borosilicate glass (1.5 mm diameter; World Precision Instruments, Sarasota, Fla.) using a two-stage puller (PP83; Narishige, Tokyo, Japan). Data were digitized, filtered (2 kHz), and acquired on-line using the programs of pClamp 9 (Axon Instruments). The pipettes were filled with a solution containing (mM): CsCl 110, $MgCl_2$ 3, EGTA 10, HEPES 10, MgATP 3, GTP 0.6. The pH was adjusted to 7.2 with CsOH. The bath solution contained (mM): $CaCl_2$ 1, $BaCl_2$ 10, HEPES 10, TEA-Cl 160, Glucose 10, TTX 0.0002 at pH (NaOH) 7.4. Whole-cell currents were elicited using 40 ms depolarizing pulses to +20 mV from a holding potential of −60 mV, applied every 15 s. To test the use-dependent inhibition, currents were elicited using 10 ms depolarizing pulses to +20 mV from a holding potential of −60 mV, applied every 0.02 s (50 Hz), 0.05 s (20 Hz), 0.1 s (10 Hz) or 15 s (0.07 Hz) respectively.

Results are presented in FIG. 2. The upper portion represents the means +/−s.e.m. of whole cell calcium current in the presence of the indicated peptide normalized to the whole cell calcium current in the same cells before application of the peptide. The lower portion of FIG. 2 shows representative whole-cell traces from which the means in the upper portion were derived. The data show that the tat portion of Tat-NR2B9c can mediate inhibition of N-type calcium channels. Mutation of the N-terminal tyrosine of Tat-NR2B9c almost completely abrogates the ability of this chimeric peptide to inhibit N-type calcium channels. The C-terminal portion of Tat-NR2B9c (KLSSIESDV (SEQ ID NO:3)), F-Tat-NR2B9c or 1994 Tat-NR2B9c K to A showed no significant inhibition of N-type calcium channel activity. Peptides 1992, 1994 and 1987 showed significant improvement in channel activity over tat alone although still displayed some reduction in the amount of N-type calcium channel activity. All of these peptides provide reduced binding to N-type calcium channels over standard Tat alone that indicate an increased therapeutic index of a drug that includes one of these Tat variant sequence.

Example 3

Dose-Dependent Reversal of Pain Hypersensitivity after Peripheral Nerve Injury with Tat-NR2B9c This example demonstrates how intravenous administration of Tat-NR2B9c reversed pain hypersensitivity in adult male Sprague-Dawley rats after peripheral nerve injury upon intravenous administration of Tat-NR2B9c in low doses (at about 100 pmol/rat). Surprisingly, intravenous administration of Tat-NR2B9c in higher doses (at about 10 mg/kg) did not result in any apparent reversal of pain hypersensitivity.

In these experiments, chronic constriction injury of the sciatic nerve was induced using the polyethylene cuff method (Mosconi T, Kruger L., Pain 1996, 64: 37-57). The left sciatic nerve of adult male Sprague-Dawley rats was exposed at mid-thigh level under halothane anesthesia. A polyethylene cuff (PE90 tubing, 2 mm in length) was slit open longitudinally and implanted around the sciatic nerve, and the animals were allowed to recover for a suitable period, e.g., 10-14 days. A sterile isotonic saline solution containing dissolved Tat-NR2B9c, or a saline-only control, was injected into the tail vein, with the animal under brief halothane anesthesia. Sensitivity to pain was measured by testing the paw withdrawal threshold of animals. Paw withdrawal thresholds to mechanical stimulation were assessed using Von-Frey filaments (Stoelting Co., Wood Dale, Ill., USA). Animals were placed in plastic cages with a plastic bottom. To test the tactile threshold required to evoke withdrawal of the stimulated paw, von Frey filaments (0.008-15.18 g) were applied perpendicularly to the plantar part of the hind paw in an ascending order. Each filament was applied for 5 times, and the paw withdrawal threshold was determined when there were three positive responses out of five times a filament was applied. To avoid tissue damage, the cut off threshold was assigned as 15.18 g.

Figure 3A:
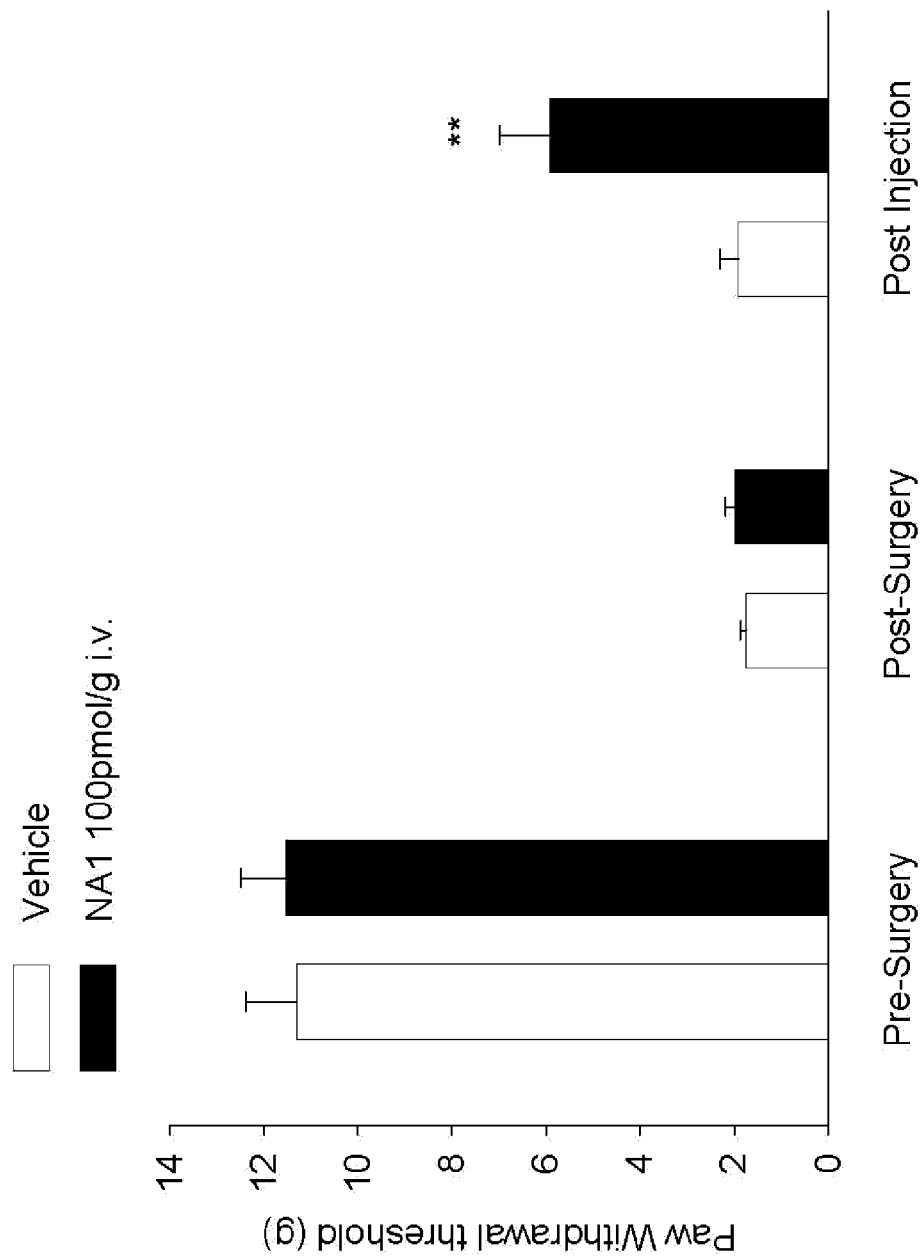
FIG. 3A: Animals treated with low doses of Tat-NR2B9c (100 pmol per animal; n=15 animals; filled bars) showed a decrease in pain hypersensitivity (i.e., an increased paw withdrawal threshold) compared to rats treated with saline vehicle alone (n=9 animals; open bars). Asterisk indicates $p<0.05$ as compared with vehicle control; the bars depict mean±SEM.

As shown in FIG. 3A, intravenous administration of Tat-NR2B9c was seen reverse pain hypersensitivity after peripheral nerve injury. Paw withdrawal threshold was tested prior to the surgical procedure used to produce the peripheral nerve (pre-surgery). On day 10-14 after the surgery (post-surgery), and just prior to administering Tat-NR2B9c or saline vehicle control, all animals showed a dramatic lowering of paw withdrawal threshold, characteristic of the pain hypersensitivity caused peripheral nerve injury. Animals were treated with Tat-NR2B9c (100 pmol per animal; n=15 animals; filled bars) or with saline vehicle (n=9 animals; open bars. *—$p<0.05$ as compared with vehicle control. The bars are mean±SEM.

Figure 3B:
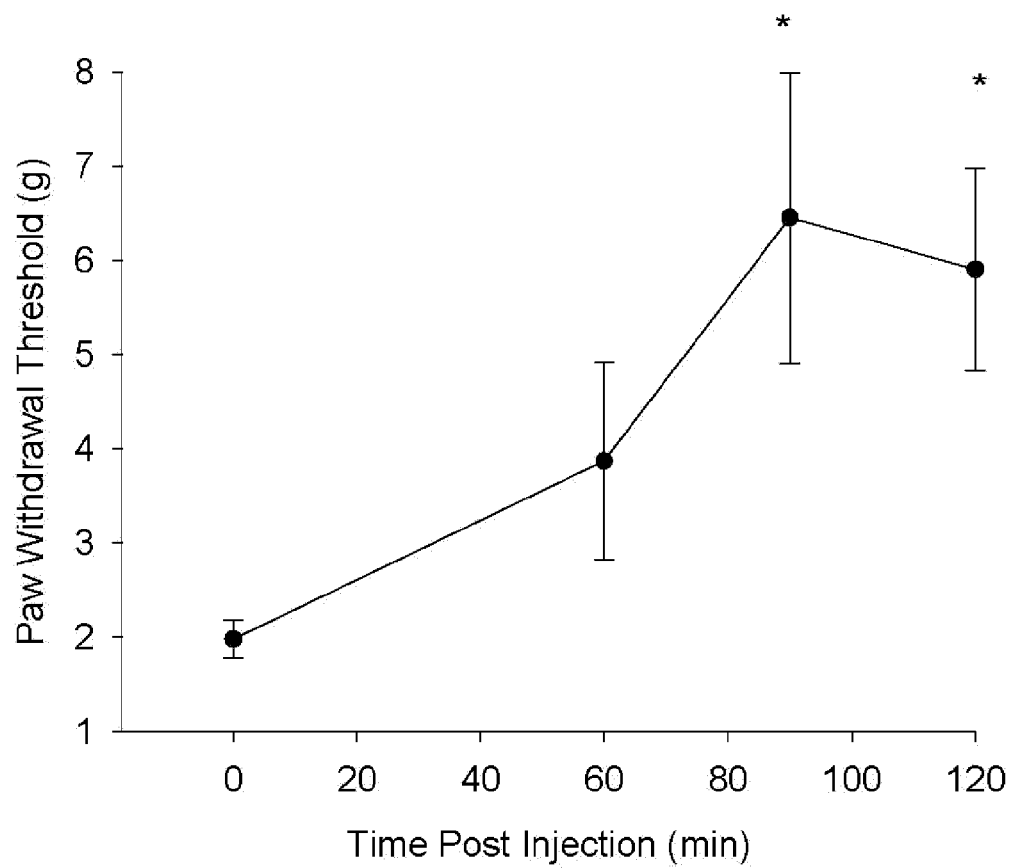
FIG. 3B: Duration of pain-alleviating effects of Tat-NR2B9c (measured in terms of reversal of pain hypersensitivity), at 0 to 2 hours post administration of Tat-NR2B9c, as measured by average paw withdrawal threshold (±SEM). Paw withdrawal threshold was measured immediately prior to Tat-NR2B9c administration (time=0) and then 60, 90 and 120 mins later (* indicates $p<0.05$ as compared with t=0).

FIG. 3B discloses the results of a time course of the reversal of pain hypersensitivity by Tat-NR2B9c. The graph shows average paw withdrawal threshold (±SEM) for animals treated with Tat-NR2B9c (100 pmol per animal i.v.) over the 2 hours after Tat-NR2B9c administration. Paw withdrawal threshold was measured immediately prior to Tat-NR2B9c administration (time=0) and then 60, 90 and 120 mins later. *—$p<0.05$ as compared with t=0.

As seen in FIG. 3C, intravenous administration of a high dose of Tat-NR2B9c (10 mg/kg i.v.) had no effect on pain hypersensitivity after peripheral nerve injury. Paw withdrawal threshold was tested prior to the surgical procedure used to produce the peripheral nerve (pre-surgery). On day 10-14 after the surgery and just prior to administering Tat-NR2B9c, all animals (n=4) showed a dramatic lowering of paw withdrawal threshold (t=0 min graph on the right), characteristic of the pain hypersensitivity caused by peripheral nerve injury. In contrast to the untreated animals, the treated animals showed no change in paw withdrawal threshold 60, 90 or 120 min after administering Tat-NR2B9c. The data are mean±SEM.

Example 4

Figure 4:
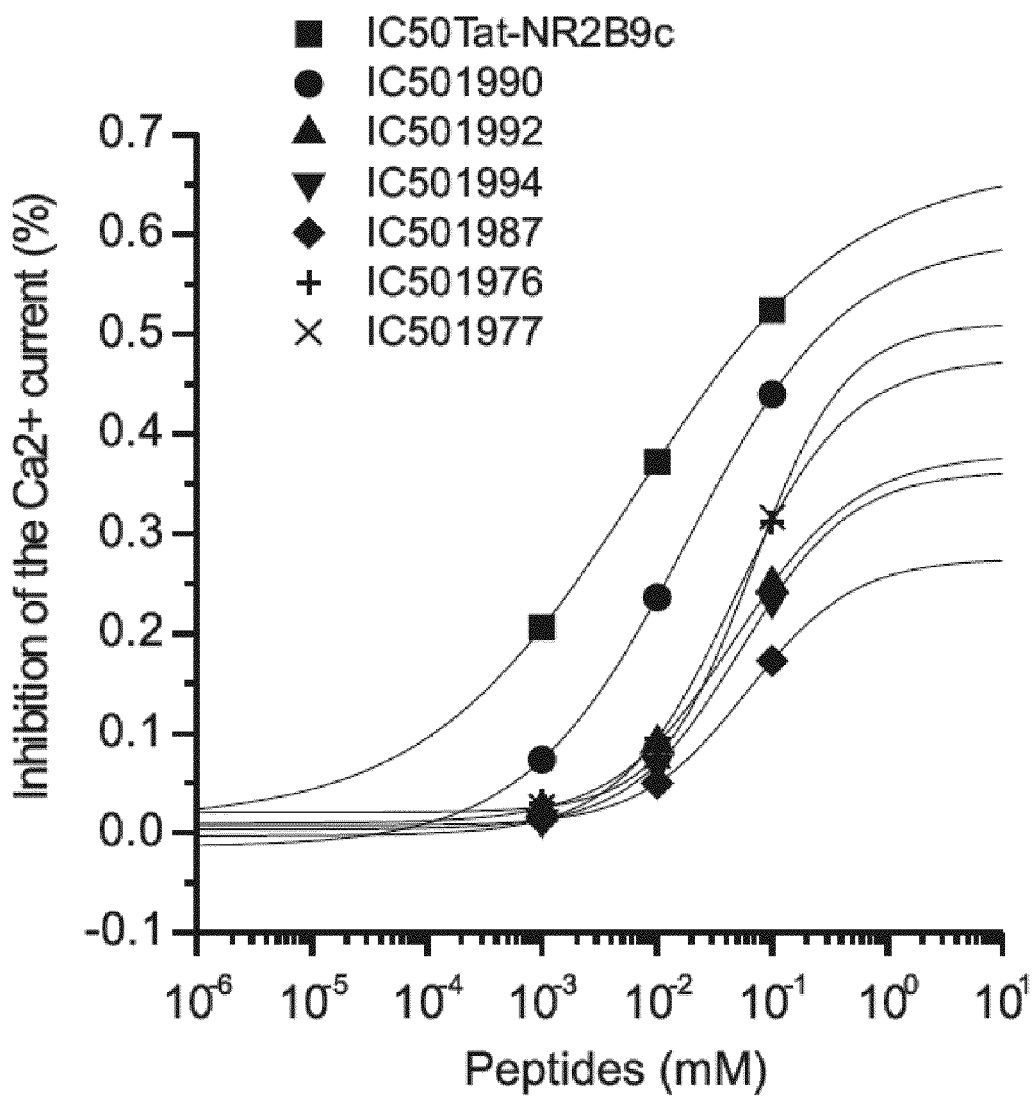
FIG. 4: $IC_{50}$ determination various peptides for N-type calcium currents in dorsal root ganglion (DRG) neurons. 1990: a Tat peptide YGRKKRRQRRR (SEQ ID NO:2); 1991: peptide 2B9c (KLSSIESDV, SEQ ID NO:3); 1992: Tat-NR2B9c-AA (YGRKKRRQRRRKLSSIEADA, SEQ ID NO:4); 1993: F-Tat-NR2B9c (FGRKKRRQRRRKLSS-IESDV, SEQ ID NO:5); 1994: Tat-NR2B9c K to A: YGRKKRRQRRRALSSIESDV, SEQ ID NO:6); 1995: F-Tat-NR2B9c K to A (FGRKKRRQRRRALSSIESDV, SEQ ID NO:7); 1976: YGRKKRRQRRRKLSSIESDX where X=norvaline (SEQ ID NO:9); 1977: YGRKKRRQR-RRKLSSIESDX where X=L-t-butyl-glycine (SEQ ID NO:10); 1987: D-isomer of Tat-NR2B9c.

Inhibition of N-type $Ca^{2+}$ Channel-Mediated Ionic Currents by Tat-NR2B9c The inhibition of N-type $Ca^{2+}$ channel-mediated ionic currents by Tat-NR2B9c was further characterized. FIG. 4 characterizes the degree of inhibition of the $Ca^{2+}$ current by Tat-NR2B9c (YGRKKRRQRRRKLSSIESDV, SEQ ID NO:1) and this is compared with the other variants: 1990 TAT (YGRKKRRQRRR, SEQ ID NO:2); 1992 Tat-NR2B9c AA (YGRKKRRQRRRKLSSIEADA, SEQ ID NO: 4); 1994 Tat-NR2B9c KtoA (YGRKKRRQRRRALSSIESDV, SEQ ID NO:6); 1987 D-Tat-NR2B9c (YGRKKRRQRRRKLSSIESDV (all D-amino acids), SEQ ID NO:8); 1976 (YGRKKRRQRRRKLSSIESDX, where X=norvaline, SEQ ID NO:9); 1977 (YGRKKRRQRRRKLSSIESDX, where X=L-t-butyl Glycine, SEQ ID NO:10).

Tissue culture: Cultures of dorsal root ganglions (DRGs) were prepared from Swiss mice at 13-14 d of gestation. Briefly, DRG's were dissected and subjected to trypsin digestion for 20 min at 37° C., mechanically dissociated and plated on cover slips coated with poly-D-lysine. They were grown in serum free MEM (Neurobasal MEM, B-27-Gibco Invitrogen Corporation, Carlsbad, Calif.). After 3-5 days, 10 µM FUDR solution was added to inhibit glial proliferation. The cultures were maintained at 37° C. in a humidified 5% $CO_2$ atmosphere and were fed twice a week. Whole-cell recording were carried out at room temperature 10-14 days after plating.

Electrophysiology recordings: Whole-cell recordings were performed with an Axopatch-1B amplifier (Axon Instruments, Foster City, Calif.) in the voltage-clamp mode. Recording electrodes, with resistances of 3-5 MΩ, were constructed from thin-walled borosilicate glass (1.5 mm diameter; World Precision Instruments, Sarasota, Fla.) using a two-stage puller (PP83; Narishige, Tokyo, Japan). Data were digitized, filtered (2 kHz), and acquired on-line using the programs of pClamp 9 (Axon Instruments). The pipettes were filled with a solution containing (mM): CsCl 110, MgCl2 3, EGTA 10, HEPES 10, MgATP 3, GTP 0.6. The pH was adjusted to 7.2 with CsOH. The bath solution contained (mM): CaCl2 1, BaCl2 10, HEPES 10, TEA-Cl 160, Glucose 10, TTX 0.0002 at pH (NaOH) 7.4. Whole-cell currents were elicited using 40 ms depolarizing pulses to +20 mV from a holding potential of −60 mV, applied every 15 s. To test the use-dependent inhibition, currents were elicited using 10 ms depolarizing pulses to +20 mV from a holding potential of −60 mV, applied every 0.02 s (50 Hz), 0.05 s (20 Hz), 0.1 s (10 Hz) or 15 s (0.07 Hz) respectively. Data analysis: Data were plotted as mean+/−s.e.m.

FIG. 4 demonstrates that increasing concentrations of all peptides containing an intact Tat sequence (YGRKKRRQRRR (SEQ ID NO:2)) significantly inhibited $Ca^{2+}$ currents in dorsal root ganglion neurons (which express predominantly N-type $Ca^{2+}$ channels). This suggests that the property of inhibiting N-type $Ca^{2+}$ channel currents resides in the Tat sequence.

Figure 5A:
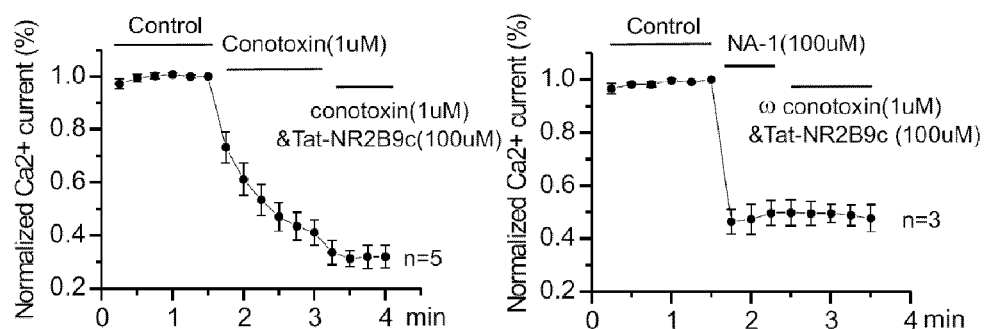
FIGS. 5A and 5B: Selectivity of Tat-NR2B9c for N-type calcium currents over L-type currents in DRG neurons.
Figure 5B:
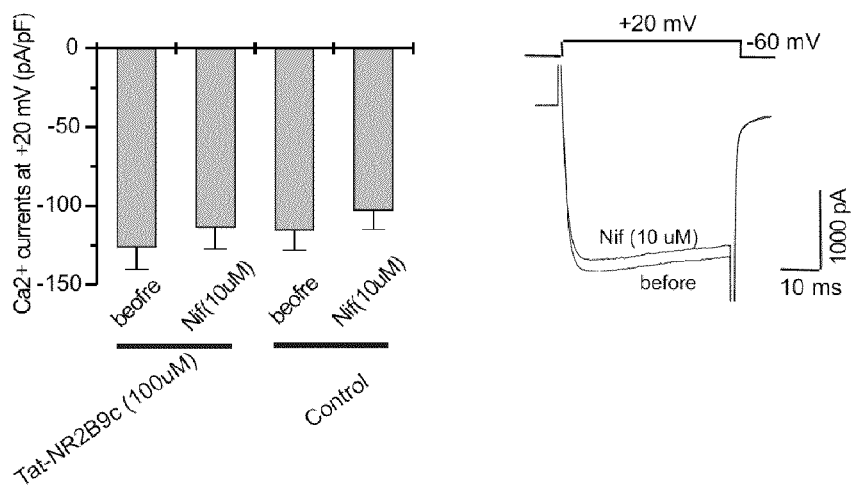

FIGS. 5A and B demonstrate inhibition of currents in DRG cells by Tat-NR2B9c in N-type $Ca^{2+}$ channels in combination with Omega conotoxin (1 µM, a selective N-type $Ca^{2+}$ channel blocker) or nifedipine (a selective L-type Ca2+ channel blocker). Omega conotoxin inhibits the $Ca^{2+}$ current, and no additional inhibition is afforded by Tat-NR2B9c (100 µM) once N-channels are blocked (FIG. 5A, left). Similarly, no additional inhibition of the current is seen when conotoxin is added after the inhibition of the ionic current by Tat-NR2B9c (FIG. 5A, right). Also, the selective L-type $Ca^{2+}$ channel blocker, nifedipine, does significantly affect the size of the $Ca^{2+}$ current recorded in the presence (100 µM intracellular), or absence of, Tat-NR2B9c as shown in FIG. 5B. The left portion of FIG. 5B shows the means +/−s.e.m.s of calcium currents, whereas on the right are representative traces of whole cell currents from a single experiment.

Figure 6:
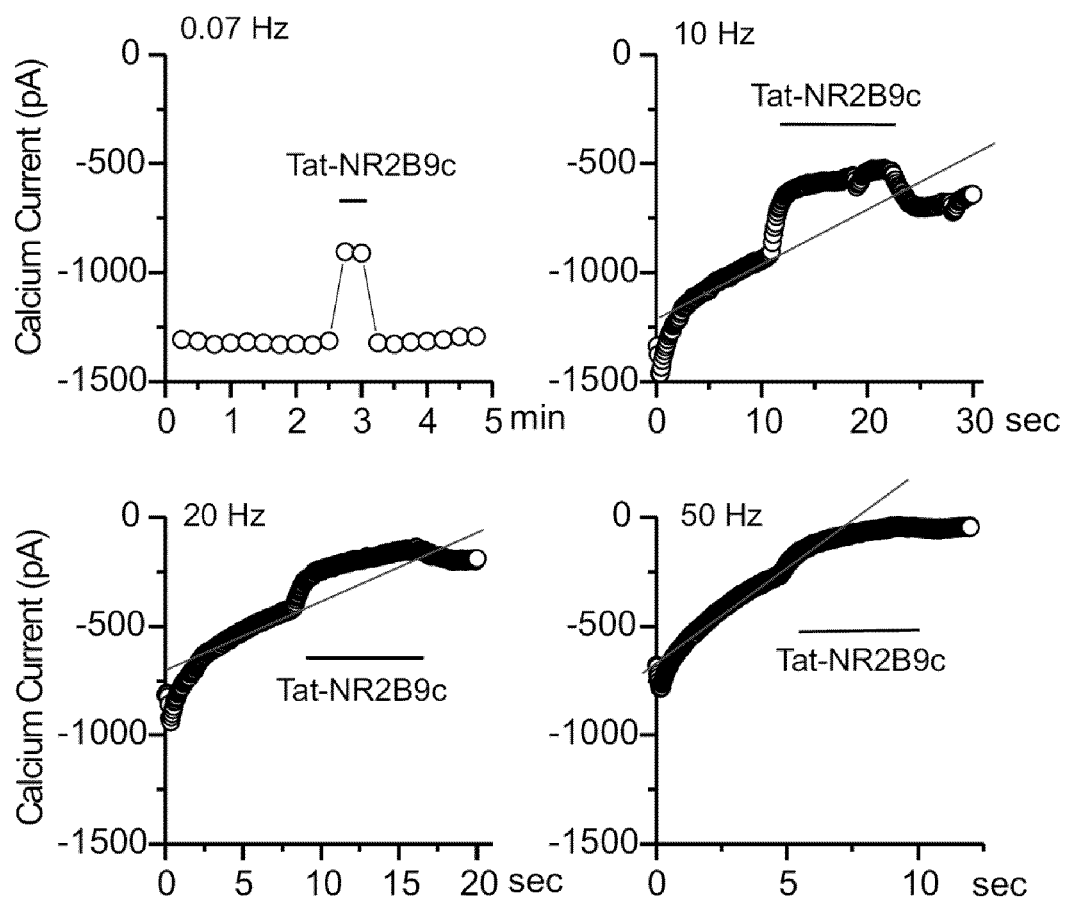
FIG. 6: Lack of use-dependence on N-type calcium current inhibition by Tat-NR2B9c. Currents were recorded in one representative DRG neuron by different frequency (0.07, 10, 20, 50 Hz). Tat-NR2B9c (100 μM) was applied as indicated. The currents showed strong frequency-dependent rundown, and the increase of frequency did not increase Tat-NR2B9c's inhibition effect.

FIG. 6 demonstrates that the block of $Ca^{2+}$ currents by Tat-NR2B9c is not frequency dependent. 100 µM Tat-NR2B9c was used to test its use-dependent effect. The currents elicited by depolarizing pulses of +20 mV showed strong frequency-dependent rundown. However, the increase of frequency (0.07, 10, 20, 50 Hz) did not increase Tat-NR2B9c' s inhibition effect on this current. The figure shows $Ca^{2+}$ currents recorded in one representative DRG neuron at different frequencies. These currents have a natural tendency to run-down after a few minutes, and the increase in frequency had no effect on the inhibition of the current by Tat-NR2B9c (representative of n=4).

Figure 7:
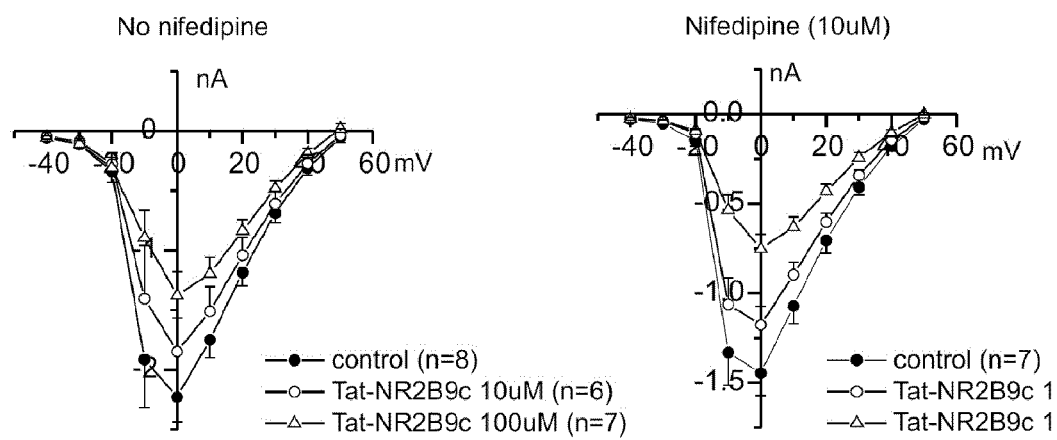
FIG. 7: Inhibition of calcium currents by Tat-NR2B9c is not voltage-dependent. The I-V relationships of $Ca^{2+}$ current in cultured DRG neurons. Tat-NR2B9c (10, 100 μM) was applied in the presence or absence of 10 μM nifedipine. The currents were elicited using 50 ms voltage-clamp steps from −40 to +50 mV from the holding potential of −60 mV.

FIG. 7 demonstrates that Tat-NR2B9c inhibits the $Ca^{2+}$ current in DRG neurons in a voltage-independent manner, and that this inhibition involves N-type $Ca^{2+}$ channels. The currents were elicited using 50 ms voltage-clamp steps from −40 to +50 mV from the holding potential of −60 mV.

In conclusion, FIGS. 4-7 show that Tat-NR2B9c can inhibit currents in DRGs, e.g., calcium currents mediated by N-type $Ca^{2+}$ channels. In addition, other peptides comprising Tat sequence can also inhibit currents. The data also show that this inhibition involves N-type $Ca^{2+}$ channels, and is independent of frequency and of voltage.

Although the foregoing invention has been described in detail for purposes of clarity of understanding, it can be obvious that certain modifications can be practiced within the scope of the appended claims. All publications, documents, accession numbers and the like cited above are hereby incorporated by reference in their entirety for all purposes to the same extent as if each were so individually denoted. If more than one version of sequence is associated with the same accession number at different times, reference to that accession number means the version associated with it at the time of filing the present application dating back to any priority application that also includes that accession number.

Unless otherwise apparent from the context, any aspect can be claimed in combination with any other, or be claimed as not present in combination with another aspect. An aspect can be for example any step, feature, property, element, mode, variable, measure, amount or embodiment. Unless otherwise apparent from the context, any language indicating that an aspect is unnecessary or optional or exemplary is intended provide adequate descriptive support for claims (e.g., under 35 U.S.C. 112 or Art. 83 and 84 of EPC) that include "exclusive" or "negative" language. Exclusive language includes any terms that specifically and explicitly limit the claims to the aspect in question. "Negative" language for example serves to explicitly exclude the aspect in question from the scope of the claims. Non-limiting examples of "exclusive" or "negative" terms include "only," "solely," "consisting of," "alone," "without", "not", "doesn't", "cannot," "in the absence of" or "excludes" or variations thereof. Non-limiting examples of language indicating that an aspect is unnecessary or optional or exemplary include terms such as "variation," "optionally," "include," "can," "may," "example," "embodiment," "aspect," "if," or variations thereof.

What is claimed is:

1. A method of treating, reducing risk of or delaying onset of pain, comprising administering a peptide having an amino acid sequence comprising YGRKKRRQRRRKLSSIESDV (SEQ ID NO:1) or a variant having fewer than four deletions, substitutions or insertions of the sequence, to a patient experiencing or at risk of pain wherein the dose is below 1 mg/kg thereby treating, reducing risk of or delaying onset of the pain; wherein the pain is neuropathic pain.

2. The method of claim 1, wherein the dose is $10^{-5}$ to $10^{-1}$ mg/kg.

3. The method of claim 1, wherein the patient is not experiencing a stroke, epilepsy, hypoxia, traumatic injury to the CNS, Alzheimer's disease, and Parkinson's disease.

4. The method of claim 1, wherein the pain is at a peripheral site.

5. The method of claim 1, wherein the pain is in the CNS.

6. The method of claim 1, wherein the peptide is administered intrathecally.

7. The method of claim 1, wherein the treatment or prophylaxis of pain is effected by binding of the peptide or peptidomimetic to an N-type calcium channel.

8. The method of claim 1, wherein residues Y, R and K of the peptide are not deleted or substituted.

9. The method of claim 1, wherein the peptide is administered intravenously.

10. A method of treating, reducing risk of or delaying onset of pain, comprising administering a tat peptide having the amino acid sequence YGRKKRRQRRR (SEQ ID NO:2) or a variant thereof having fewer than 4 deletions, substitutions or insertions of the sequence and fewer than five flanking residues at each end, to a patient experiencing or at risk of pain thereby treating, reducing risk of or delaying onset of the pain.

11. The method of claim 10, wherein the dose is below 1 mg/kg.

12. The method of claim 10, wherein the dose is $10^{-5}$ to $10^{-1}$ mg/kg.

13. The method of claim 10, wherein the patient is not experiencing a stroke, epilepsy, hypoxia, traumatic injury to the CNS, Alzheimer's disease, and Parkinson's disease.

14. The method of claim 10, wherein the pain is at a peripheral site.

15. The method of claim 10, wherein the pain is in the CNS.

16. The method of claim 10, wherein the tat peptide is administered intrathecally.

17. The method of claim 10, wherein the regime predominantly results in inhibition of N-type calcium channels rather than inhibition of PSD-95 interactions with NMDAR or NOS.

18. The method of claim 10, wherein residues Y, R and K of the peptide are not deleted or substituted.

19. A method of treating, reducing risk of or delaying onset of delaying onset of pain, comprising administering a peptide having an amino acid sequence comprising YGRKKRRQRRRKLSSIESDV (SEQ ID NO:1) or a variant having fewer than four deletions, substitutions or insertions of the sequence, to a patient experiencing or at risk of pain wherein the dose is below 1 mg/kg thereby treating, reducing risk of or delaying onset or of the pain; wherein the pain is at a peripheral site and is not non-cardiac associated chest pain.

* * * * *

SEQUENCE LISTING

<160> NUMBER OF SEQ ID NOS: 19

<210> SEQ ID NO 1
<211> LENGTH: 20
<212> TYPE: PRT
<213> ORGANISM: Artificial Sequence
<220> FEATURE:
<223> OTHER INFORMATION: Synthetic peptide Tat-NR2B9c

<400> SEQUENCE: 1

Tyr Gly Arg Lys Lys Arg Arg Gln Arg Arg Lys Leu Ser Ser Ile
 1               5                  10                  15

Glu Ser Asp Val
            20

<210> SEQ ID NO 2
<211> LENGTH: 11
<212> TYPE: PRT
<213> ORGANISM: Artificial Sequence
<220> FEATURE:
<223> OTHER INFORMATION: synthetic 1990: a Tat peptide

<400> SEQUENCE: 2

Tyr Gly Arg Lys Lys Arg Arg Gln Arg Arg Arg
 1               5                  10

<210> SEQ ID NO 3
<211> LENGTH: 9
<212> TYPE: PRT
<213> ORGANISM: Artificial Sequence
<220> FEATURE:
<223> OTHER INFORMATION: synthetic 1991: peptide 2B9c

<400> SEQUENCE: 3

Lys Leu Ser Ser Ile Glu Ser Asp Val
 1               5

<210> SEQ ID NO 4
<211> LENGTH: 20
<212> TYPE: PRT
<213> ORGANISM: Artificial Sequence
<220> FEATURE:
<223> OTHER INFORMATION: synthetic 1992: peptide Tat-NR2B9c-AA

<400> SEQUENCE: 4

Tyr Gly Arg Lys Lys Arg Arg Gln Arg Arg Lys Leu Ser Ser Ile
 1               5                  10                  15

Glu Ala Asp Ala
            20

<210> SEQ ID NO 5
<211> LENGTH: 20
<212> TYPE: PRT
<213> ORGANISM: Artificial Sequence
<220> FEATURE:
<223> OTHER INFORMATION: synthetic 1993: peptide F-Tat-NR2B9c

<400> SEQUENCE: 5

Phe Gly Arg Lys Lys Arg Arg Gln Arg Arg Lys Leu Ser Ser Ile
 1               5                  10                  15

Glu Ser Asp Val
            20

<210> SEQ ID NO 6

```
<211> LENGTH: 20
<212> TYPE: PRT
<213> ORGANISM: Artificial Sequence
<220> FEATURE:
<223> OTHER INFORMATION: synthetic 1994: peptide Tat-NR2B9c K to A

<400> SEQUENCE: 6

Tyr Gly Arg Lys Lys Arg Arg Gln Arg Arg Arg Ala Leu Ser Ser Ile
1               5                   10                  15

Glu Ser Asp Val
            20

<210> SEQ ID NO 7
<211> LENGTH: 20
<212> TYPE: PRT
<213> ORGANISM: Artificial Sequence
<220> FEATURE:
<223> OTHER INFORMATION: synthetic 1995: peptide F-Tat-NR2B9c K to A

<400> SEQUENCE: 7

Phe Gly Arg Lys Lys Arg Arg Gln Arg Arg Arg Ala Leu Ser Ser Ile
1               5                   10                  15

Glu Ser Asp Val
            20

<210> SEQ ID NO 8
<211> LENGTH: 20
<212> TYPE: PRT
<213> ORGANISM: Artificial Sequence
<220> FEATURE:
<223> OTHER INFORMATION: synthetic 1987: D-isomer of Tat-NR2B9c

<400> SEQUENCE: 8

Tyr Gly Arg Lys Lys Arg Arg Gln Arg Arg Arg Lys Leu Ser Ser Ile
1               5                   10                  15

Glu Ser Asp Val
            20

<210> SEQ ID NO 9
<211> LENGTH: 20
<212> TYPE: PRT
<213> ORGANISM: Artificial Sequence
<220> FEATURE:
<223> OTHER INFORMATION: synthetic 1976: peptide Tat-NR2B9c
<220> FEATURE:
<221> NAME/KEY: MOD_RES
<222> LOCATION: 20
<223> OTHER INFORMATION: Xaa = norvaline

<400> SEQUENCE: 9

Tyr Gly Arg Lys Lys Arg Arg Gln Arg Arg Arg Lys Leu Ser Ser Ile
1               5                   10                  15

Glu Ser Asp Xaa
            20

<210> SEQ ID NO 10
<211> LENGTH: 20
<212> TYPE: PRT
<213> ORGANISM: Artificial Sequence
<220> FEATURE:
<223> OTHER INFORMATION: synthetic 1977: peptide Tat-NR2B9c
<220> FEATURE:
<221> NAME/KEY: MOD_RES
<222> LOCATION: 20
<223> OTHER INFORMATION: Xaa = L-t-butyl-glycine

<400> SEQUENCE: 10
```

```
Tyr Gly Arg Lys Lys Arg Arg Gln Arg Arg Lys Leu Ser Ser Ile
1               5                   10                  15

Glu Ser Asp Xaa
            20
```

<210> SEQ ID NO 11
<211> LENGTH: 5
<212> TYPE: PRT
<213> ORGANISM: Artificial Sequence
<220> FEATURE:
<223> OTHER INFORMATION: synthetic linker peptide

<400> SEQUENCE: 11

```
Gly Ser Ser Ser Ser
1               5
```

<210> SEQ ID NO 12
<211> LENGTH: 5
<212> TYPE: PRT
<213> ORGANISM: Artificial Sequence
<220> FEATURE:
<223> OTHER INFORMATION: synthetic linker peptide

<400> SEQUENCE: 12

```
Thr Gly Glu Lys Pro
1               5
```

<210> SEQ ID NO 13
<211> LENGTH: 8
<212> TYPE: PRT
<213> ORGANISM: Artificial Sequence
<220> FEATURE:
<223> OTHER INFORMATION: synthetic linker peptide

<400> SEQUENCE: 13

```
Gly Gly Arg Arg Gly Gly Gly Ser
1               5
```

<210> SEQ ID NO 14
<211> LENGTH: 9
<212> TYPE: PRT
<213> ORGANISM: Artificial Sequence
<220> FEATURE:
<223> OTHER INFORMATION: synthetic linker peptide

<400> SEQUENCE: 14

```
Leu Arg Gln Arg Asp Gly Glu Arg Pro
1               5
```

<210> SEQ ID NO 15
<211> LENGTH: 86
<212> TYPE: PRT
<213> ORGANISM: Human immunodeficiency virus 1
<220> FEATURE:
<223> OTHER INFORMATION: representative tat protein

<400> SEQUENCE: 15

```
Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Ala His Gln Asn Ser Gln Thr
    50                  55                  60
```

His Gln Ala Ser Leu Ser Lys Gln Pro Thr Ser Gln Pro Arg Gly Asp
 65                  70                  75                  80

Pro Thr Gly Pro Lys Glu
                 85

<210> SEQ ID NO 16
<211> LENGTH: 10
<212> TYPE: PRT
<213> ORGANISM: Artificial Sequence
<220> FEATURE:
<223> OTHER INFORMATION: synthetic tat peptide

<400> SEQUENCE: 16

Tyr Gly Arg Lys Lys Arg Arg Gln Arg Arg
 1               5                  10

<210> SEQ ID NO 17
<211> LENGTH: 5
<212> TYPE: PRT
<213> ORGANISM: Artificial Sequence
<220> FEATURE:
<223> OTHER INFORMATION: synthetic tat peptide

<400> SEQUENCE: 17

Tyr Gly Arg Lys Lys
 1               5

<210> SEQ ID NO 18
<211> LENGTH: 19
<212> TYPE: PRT
<213> ORGANISM: Artificial Sequence
<220> FEATURE:
<223> OTHER INFORMATION: synthetic antennapedia internalization peptide

<400> SEQUENCE: 18

Ser Gly Arg Gln Ile Lys Ile Trp Phe Gln Asn Arg Arg Met Lys Trp
 1               5                  10                  15

Lys Lys Cys

<210> SEQ ID NO 19
<211> LENGTH: 26
<212> TYPE: PRT
<213> ORGANISM: Artificial Sequence
<220> FEATURE:
<223> OTHER INFORMATION: synthetic analgesic drug; Ziconotide

<400> SEQUENCE: 19

Cys Lys Gly Lys Gly Ala Lys Cys Ser Arg Leu Met Tyr Asp Cys Cys
 1               5                  10                  15

Thr Gly Ser Cys Arg Ser Gly Lys Cys Gly
             20                  25